United States Patent [19]

Pearson

[11] 4,252,808

[45] Feb. 24, 1981

[54] β-LACTAM ANTIBACTERIAL AGENTS, THEIR USE IN PHARMACEUTICAL COMPOSITIONS, THE PROCESS FOR THEIR PREPARATION AND INTERMEDIATES FOR USE IN THAT PROCESS

[75] Inventor: Michael J. Pearson, Horsham, England

[73] Assignee: Beecham Group Limited, United Kingdom

[21] Appl. No.: 15,006

[22] Filed: Feb. 26, 1979

[30] Foreign Application Priority Data

Mar. 4, 1978 [GB] United Kingdom ............... 08669/78

[51] Int. Cl.³ .................. A61K 31/505; C07D 487/14
[52] U.S. Cl. ............................... 424/251; 260/239 A; 544/251
[58] Field of Search ......................... 544/251; 424/251

[56] References Cited

U.S. PATENT DOCUMENTS 4,138,553  2/1979  Ishimoto et al. ...................... 544/18

Primary Examiner—Paul M. Coughlan, Jr.
Attorney, Agent, or Firm—Jacobs & Jacobs

[57] ABSTRACT

The compounds of the formula (I):

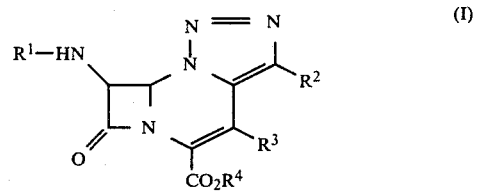

wherein $R^1$ is a hydrogen atom, a trityl group or an acyl group as found in known antibacterially active penicillins or cephalosporins; $R^2$ is a hydrogen atom, a lower alkyl group or an aryl group; $R^3$ is a hydrogen atom, a lower alkyl group, a substituted lower alkyl or a thiosubstituted lower alkyl group; and $R^4$ is a group such that $CO_2R^4$ is a carboxylic acid group or a salt or readily removable ester thereof; are antibiotics. The compounds may be formulated in pharmaceutical compositions.

Processes for the preparation of the compounds (I) are also described.

10 Claims, No Drawings

β-LACTAM ANTIBACTERIAL AGENTS, THEIR USE IN PHARMACEUTICAL COMPOSITIONS, THE PROCESS FOR THEIR PREPARATION AND INTERMEDIATES FOR USE IN THAT PROCESS

β-Lactam antibiotics such as penicillins and cephalosporins are bicyclic structures which contain a β-lactam ring fused to a further ring. A group of tricyclic β-lactam antibiotics has now been discovered.

Accordingly the present invention provides the compounds of the formula (I):

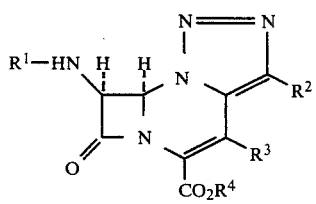

wherein $R^1$ is a hydrogen atom, a trityl group or an acyl group as found in known antibacterially active penicillins or cephalosporins; $R^2$ is a hydrogen atom, a lower alkyl group or an aryl group; $R^3$ is a hydrogen atom, a lower alkyl group, a substituted lower alkyl or a thiosubstituted lower alkyl group; and $R^4$ is a group such that $CO_2R^4$ is a carboxylic acid group or a salt or readily removable ester thereof.

When used herein the term "lower" means that the group contains up to 4 carbon atoms. When used herein the term "substituted" means substituted by a $CO_2R^4$ or $OR^5$ group where $R^4$ is as defined above and $R^5$ is a lower alkyl or lower acyl group. When used herein the term "aryl" means phenyl, pyridyl or phenyl substituted by a fluorine, chlorine, or bromine atom or a nitro, lower alkyl, lower alkoxyl, carboxylic acid group or a lower alkyl or benzyl ester thereof. When used herein the term "thio-substituted" means substituted by a group $SR^7$, where $R^7$ is a 5-membered heteroaromatic ring containing up to 4 heteroatoms any of which may be N, and one of which may be O or S and which may be optionally substituted by a lower alkyl group or a substituted lower alkyl group.

Those compounds of the formula (I) wherein $R^1$ is a hydrogen atom are intended mainly as intermediates in the preparation of corresponding compounds of the formula (I) wherein $R^1$ is an acyl group.

Those compounds of the formula (I) wherein $R^1$ is a trityl group are intended mainly as intermediates in the preparation of corresponding compounds of the formula (I) wherein $R^1$ is a hydrogen atom.

Those compounds of the formula (I) wherein $CO_2R^4$ is an esterified carboxyl group are primarily intended as intermediates in the preparation of a corresponding compound of the formula (I) wherein $CO_2R^4$ is a carboxylic acid group or a salt thereof.

From the foregoing it will be realised that the antibacterially active compounds of this invention can be represented by the formula (II):

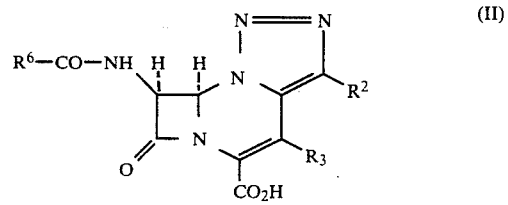

and salts thereof wherein $R^2$ and $R^3$ are as defined in relation to formula (I) and $R^6$ is a group such that $R^6$—CO—NH— is an acylamino group as found in known antibacterially active penicillins or cephalosporins.

Suitable values for $R^2$ in the compounds of the formulae (I) and (II) include the hydrogen atom and methyl, ethyl, propyl, butyl, phenyl, p-nitrophenyl, p-methoxycarbonylphenyl and the like. Favoured values for $R^2$ include the hydrogen atom and the methyl and ethyl groups. The preferred value for $R^2$ is the hydrogen atom.

Suitable values for $R^3$ in the compounds of the formulae (I) and (II) include the hydrogen atom and methyl, ethyl, propyl, butyl, acetoxymethyl and the like, such as those specifically described in the Examples herein.

Favoured values for $R^3$ include the methyl, ethyl, and acetoxymethyl group. The preferred value for $R^3$ is the methyl group.

From the foregoing it will be realised that certain particularly favoured antibacterially active compounds of this invention are those of the formula (III):

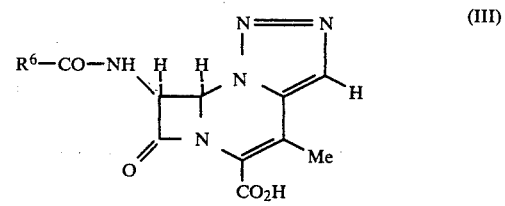

and salts thereof wherein $R^6$ is as defined in relation to formula (II).

Suitable groups $R^6CO$ for inclusion in the compounds of the formula (II) and (III) include those of the subformulae (a)–(d):

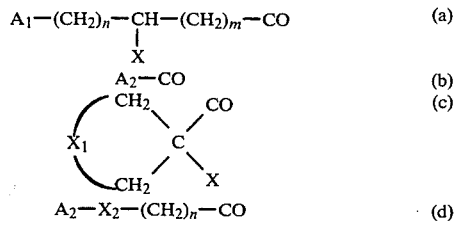

wherein n is 0, 1 or 2; m is 0, 1 or 2; $A_1$ is $C_1$–$C_6$ alkyl, $C_3$–$C_6$ cycloalkyl, cyclohexenyl, cyclohexadienyl, phenyl, hydroxy-phenyl, thienyl or pyridyl group; X is a hydrogen or halogen atom, a carboxylic acid, carboxylic ester, azido, tetrazolyl, hydroxy, acyloxy, amino, unreido, guanidino or acylureido group; $A_2$ is an aromatic group each as a phenyl, a 2,6-dimethoxyphenyl, 2-alkoxy-1-naphthyl, 3-arylisoxazolyl or 3-aryl-5-methylisoxazolyl group; $X_1$ is a $CH_2OCH_2$, $CH_2SCH_2$ or $(CH_2)_n$ group; $X_2$ is an oxygen or sulphur atom.

Favoured groups $R^6$ for inclusion in the compounds of the formulae (II) and (III) include those of the subformulae (e) and (f):

$$R^8-\underset{R^9}{\overset{|}{CH}}-\quad (e)$$

$$R^{10}-\underset{R^{11}}{\overset{|}{CH}}-\quad (f)$$

wherein $R^8$ is a phenyl, thienyl or phenoxy group; $R^9$ is a hydrogen atom or methyl group; $R^{10}$ is a phenyl, p-hydroxyphenyl, thienyl or cyclohexadienyl group; and $R^{11}$ is a hydroxyl, amino or carboxylic acid group or lower alkyl or phenyl, tolyl or indanyl ester thereof.

One apt group of the sub-formula (e) is the phenoxymethyl group. A second apt group of the subformula (e) is the benzyl group. A third apt group of the sub-formula (e) is the thienylmethyl group.

One suitable group of the formula $R^6CO$ is the D-phenylglycyl group.

Another suitable group of the formula $R^6CO$ is the D-p-hydroxyphenylglycyl group.

Another suitable group of the formula $R^6CO$ is the D-mandelyl group.

Another suitable group of the formula $R^6CO$ is the malonyl group.

Another suitable group of the formula $R^6CO$ is the benzoyl group.

Another suitable group of the formula $R^6CO$ is the 2-thienylacetyl group.

Another suitable group of the formula $R^6CO$ is the 3-thienylacetyl group.

Another suitable group of the formula $R^6 CO$ is the 2-thienyl-α-carboxyacetyl group.

Another suitable group of the formula $R^6CO$ is the 3-thienyl-α-carboxyacetyl group.

Another suitable group of the formula $R^6CO$ is the phenoxyacetyl group.

One group of novel intermediates of this invention is that of the formula (IV):

(IV)

wherein $R^2$ and $R^3$ are as defined in relation to formula (I) and $R^{12}$ is a group such that $CO_2R^{12}$ is an ester which is readily convertible to a carboxylic acid or a salt thereof.

Particularly apt values for $R^2$ and $R^3$ are those referred to in relation to formula (II).

A particularly favoured group $R^{12}$ is the tertiary butyl group.

A further particularly favoured group $R^{12}$ is the benzyl group.

A further group of novel intermediates of this invention is that of the formula (V):

(V)

and salts thereof wherein $R^2$, $R^3$ and $R^{12}$ are as defined in relation to formula (IV).

The compounds of this invention may be in the form of an alkali metal, alkaline earth metal or nitrogenous base salt or the like. Particularly suitable salts include the sodium, potassium, ammonium and the like salts. A preferred salt is the sodium salt.

The compounds of this invention which contain a basic group in the acylamino side chain can also form acid addition salts with pharmaceutically acceptable acids such as hydrochloric, or other strong acids. Most suitably those compounds which contain a basic group in the acylamino side chain are in zwitterionic form.

Intermediates of this invention may be esterified for example by a tertiary butyl group or like acid labile group or by a benzyl, p-nitrobenzyl or like hydrogenolysable group.

The antibacterial agents of this invention may be in the form of in-vivo hydrolysable esters.

Examples of suitable in vivo hydrolysable esters of the compounds of this invention include those which break down readily in the human body to leave the parent acid or its salt, for example acyloxyalkyl esters such as acetoxymethyl, pivaloyloxymethyl, α-acetoxyethyl, α-acetoxybenzyl, α-pivaloyloxyethyl, 60-ethoxycarbonyloxyethyl esters and lactone esters such as the phthalidyl esters.

The present invention also provides antibacterial pharmaceutical compositions which comprise a compound of the formula (II) together with a pharmaceutically acceptable carrier.

The compositions of this invention are normally adapted for administration to humans. Such compositions may be formulated in a conventional manner for antibacterial agents, for example, in a similar manner to known penicillins or cephalosporins. Unit dose formulations according to this invention will normally contain from 100 mg to 4000 mg, more usually from 125 mg to 1000 mg and generally from 250 mg to 500 mg of a compound of the formula (II).

The compounds of this invention may be provided in orally administrable form, for example as tablets or capsules.

The compounds of this invention may be provided in a form suitable for administration by injection or infusion, for example in the form of a sterile salt such as the sterile sodium salt sealed in a vial or ampule or the like.

The compositions of this invention may be used to treat infections due to susceptible bacteria in humans and in domestic animals. Thus for example humans may be treated for diseases due to gram-positive microorganisms such as *Staphylococcus aureus*. Similarly, the compositions may be used for the treatment of mastitis in cattle, for example by intramammary administration.

The compounds of this invention may be prepared according to the sequences outlined in Schemes 1-6:

Scheme 1
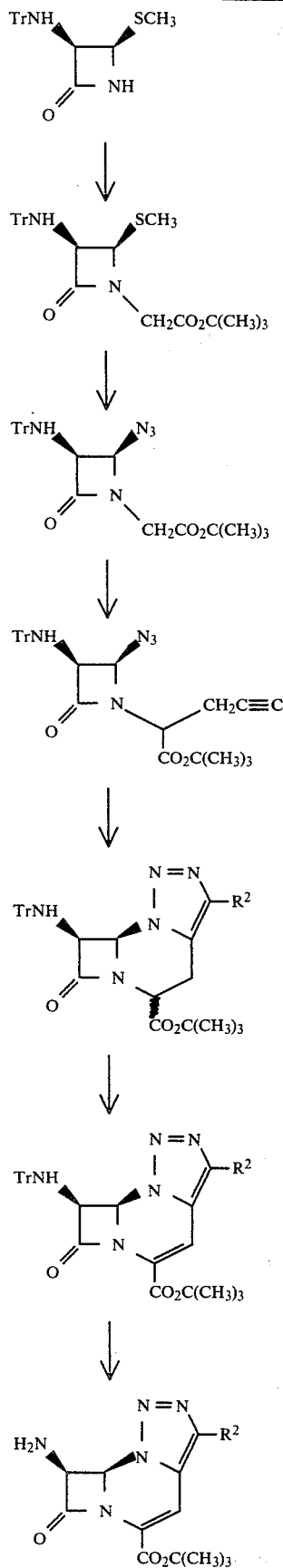
Scheme 2
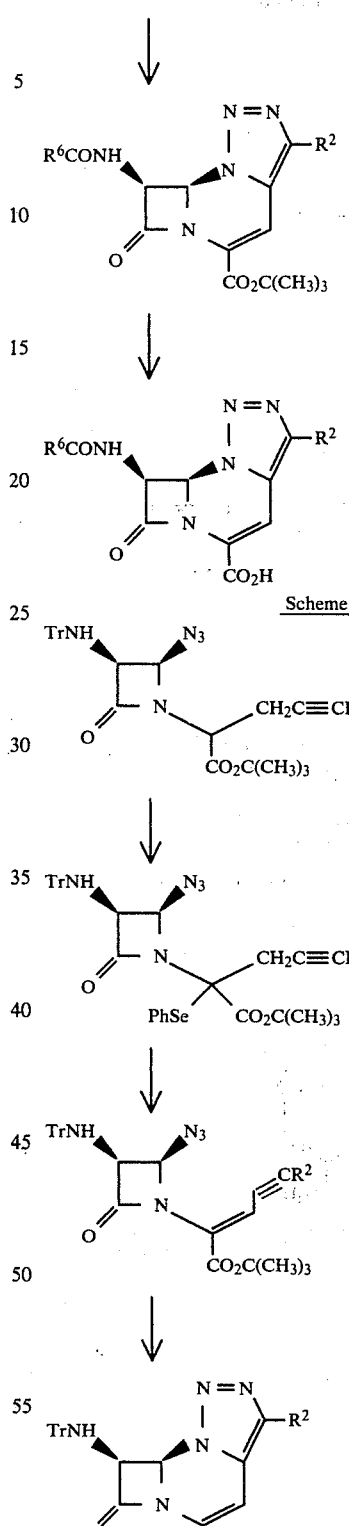
Scheme 3

7
-continued
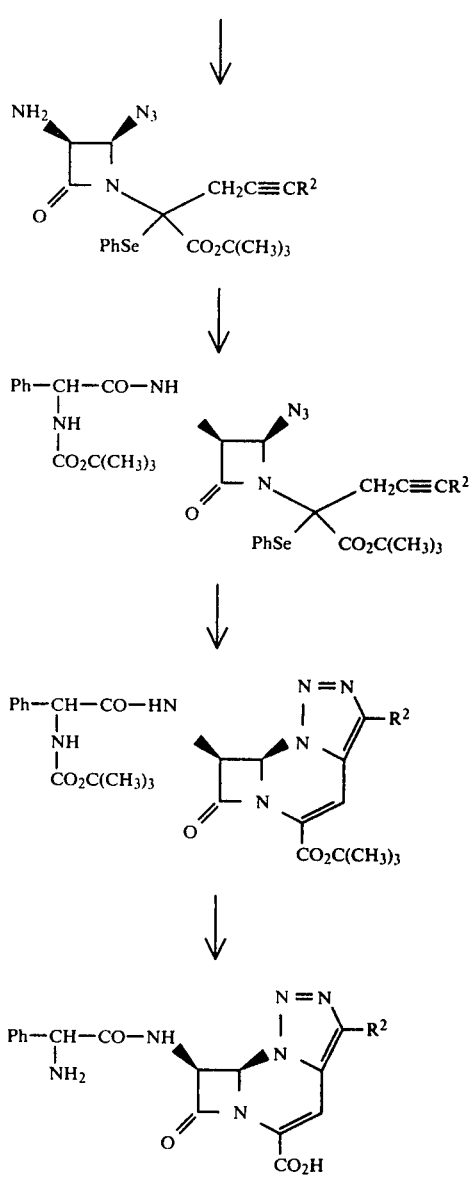
Scheme 4
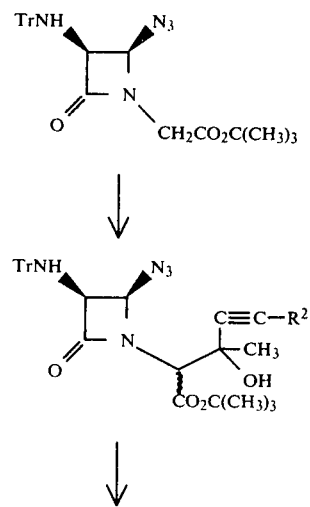
8
-continued
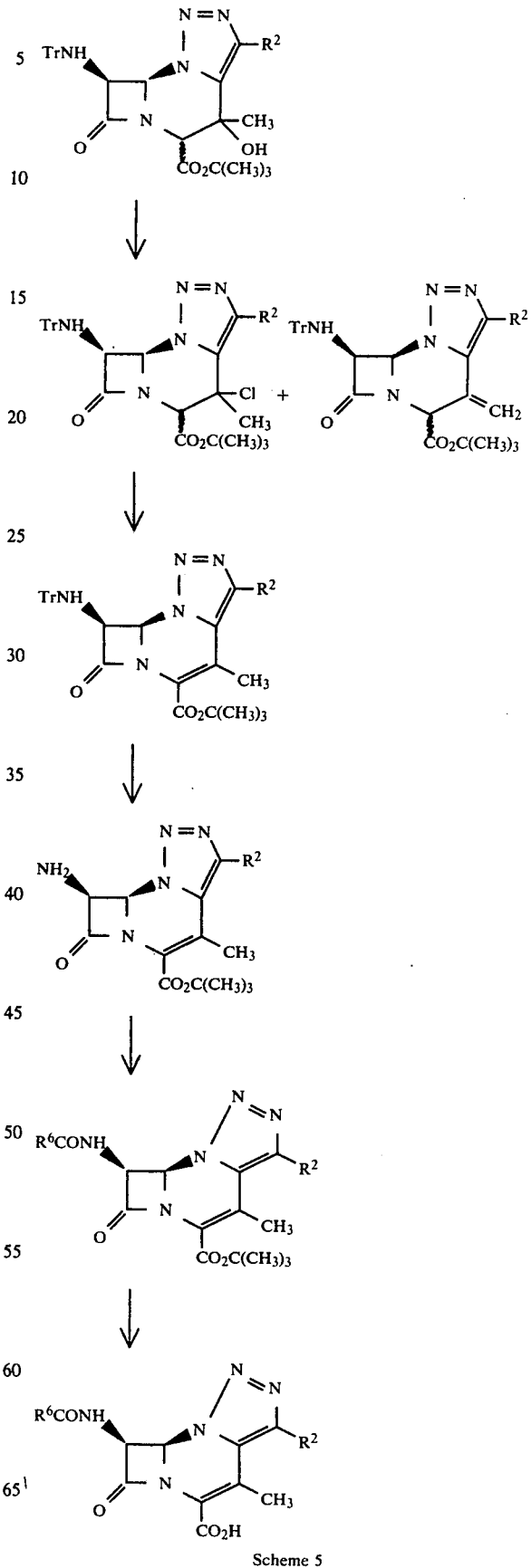
Scheme 5

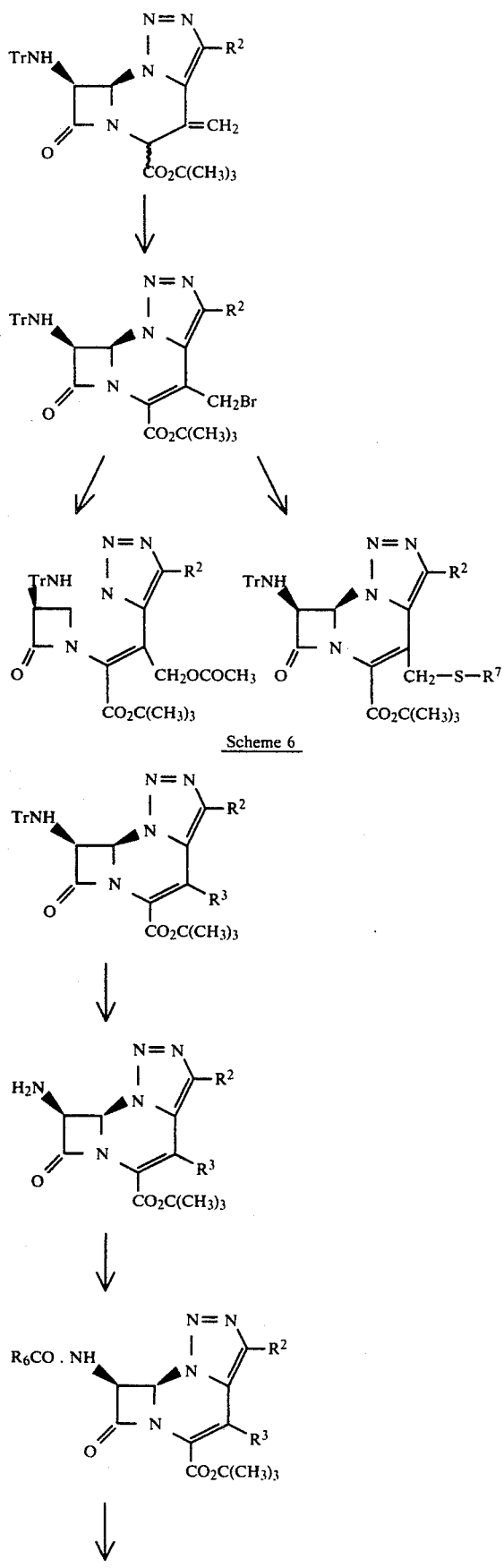

Scheme 6

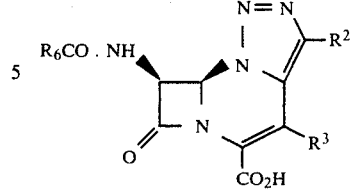

The present invention provides a process for the preparation of the compounds of the formula (II) as hereinbefore defined which process comprises the acylation of a corresponding compound of the formula (V) as hereinbefore defined with a reactive acylating derivative of a carboxylic acid of the formula (VI):

$$R^6-CO_2H \qquad (VI)$$

wherein $R^6$ is as defined in relation to formula (II) and in which any acylatable group is optionally protected and thereafter performing one or more of the following reactions:

(a) removing any protecting group from the group $R^6$ (b) hydrolysing or hydrogenolysing the ester group $CO_2R^{12}$ to yield a free or salted carboxylic group.

The term "acylating derivative of a carboxylic acid" means any N-acylating compound known to be suitable for the performance of analogous reactions with 6-aminopenicillanic acid, 7-aminocephalosporanic acid, 7-aminodesacetoxycephalosporanic acid or salt, silyl derivative or ester thereof. Reactive groups present in such acylating agents may be protected in conventional manner as will be well understood by those skilled in the arts of preparing semi-synthetic penicillins or cephalosporins.

A particularly suitable group $R^{12}$ is the t-butyl group which may be removed by such conventional procedures as reaction with an anhydrous acid such as trifluoroacetic acid, for example at an approximately ambient temperature optionally in the presence of an inert solvent.

The intermediates of the formula (V) may be prepared by the replacement of the triphenylmethyl group from a corresponding compound of the formula (IV). In general this may be accomplished by mild acid hydrolysis at a depressed temperature, for example by the use of p-toluene-sulphonic acid at 0° to −20° C. in an organic solvent such as methylene chloride or the like.

The preparation and reaction of the intermediates may be prepared by the general methods of the preceding reaction schemes and as described in the Examples hereinafter.

In a further aspect this invention provides the useful intermediates of the formula (VII):

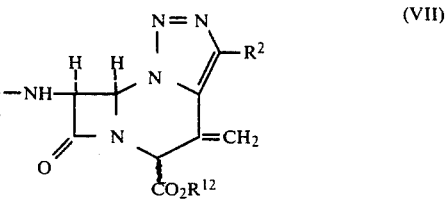

wherein $R^1$ and $R^2$ are as defined in relation to formula (I) and $R^{12}$ is defined in relation to formula (V).

In such compounds R¹ is most suitably a trityl group; R² is a hydrogen atom and R¹² is a tertiary butyl group.

Reaction of a compound of the formula (VII) in an inert solvent at a depressed temperature with a non-nucleophilic base causes isomerisation to the corresponding compounds containing an endocyclic (as opposed to the exocyclic) double bond with a methyl group at the 8-position.

In yet a further aspect this invention provides the useful intermediates of the formula (VIII):

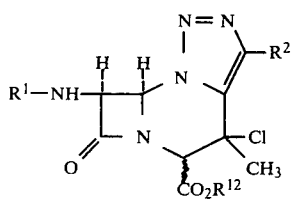
(VIII)

wherein R¹ and R² are as defined in relation to formula (I) and R¹² is as defined in relation to formula (I).

In such compounds R¹ is most suitably a trityl group; R² is a hydrogen atom; and R¹² is a tertiary butyl group.

Reaction of a compound of the formula (VIII) with a base as described in relation to reaction of a compound of the formula (VII), also leads to the preparation of compound possessing an endocyclic double bond and a methyl group at the 8-position.

The useful intermediates of the formula (VII) may be converted into the corresponding 8-bromomethyl compound by reaction with dibromodiethylmalonate in an aprotic solvent such a tetrahydrofuran at a depressed temperature such as −80° to −40° C. The resulting 8-bromomethyl compound may be used as an intermediate in conventional displacement reactions in conventional displacement reactions in which the bromine atom is replaced by the residue of an oxygen or sulphur nucleophile.

The sequence below has been described in the literature (E. G. Brain, A. J. Eglington, J. H. C. Nayler, M. J. Pearson, and R. Southgate J. C. S. Perkin 1, 1976, 447). See also British Pat. No. 1,355,330.

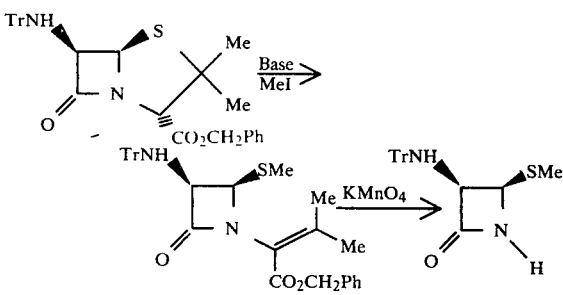

EXAMPLE 1 t-Butyl 2-[(3R,4R)-4-methylthio-2-oxo-3-triphenylmethylaminoazetidin-1-yl]acetate (2)

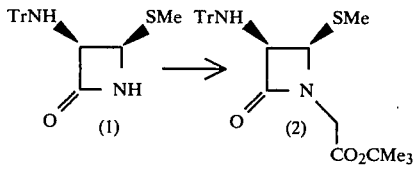

(3R,4R)-4-Methylthio-3-triphenylmethylaminoazetidin-2-one [(1); 15 g] was dissolved in dry dimethylformamide (225 ml), containing t-butyl bromoacetate (9.24 g) and powdered anhydrous potassium carbonate (9.9 g). The mixture was vigorously stirred at room temperature for 20 h., and then poured into ethyl acetate/brine. The organic layer was separated, washed successively with water and brine, dried and evaporated. Trituration with ether and filtration provided the product [(2); 10 g]. Chromatography of the mother liquors on silica afforded further material (4.8 g). m.p. 147°–149° (ethyl acetate/petroleum ether). $[\alpha]_D^{23}$ −49.9° (c=1 in chloroform). νmax (Nujol) 3300, 1758, 1740 cm⁻¹. δppm (CDCl₃) 1.35 (9H, s), 1.65 (3H, s), 2.85 (1H, d, 7 Hz, exch), 3.4 and 4.05 (2H, AB_q, J 17 Hz), 4.11–4.58 (2H, m), 7.0–7.7 (15H, m). (Found: C, 71.2; H, 6.4; N, 5.7; S, 6.8; $C_{29}H_{32}N_2O_3S$ requires C, 71.3; H, 6.6; N, 5.7; S, 6.6%).

EXAMPLE 2 t-Butyl 2-[3S,4R]-4-azido-2-oxo-3-triphenylmethylaminoazetidin-1-yl]-acetate (3) and t-butyl 2-[(3S,4S)-4-azido-2-oxo-3-triphenylmethylaminoazetidin-1-yl]acetate (4)

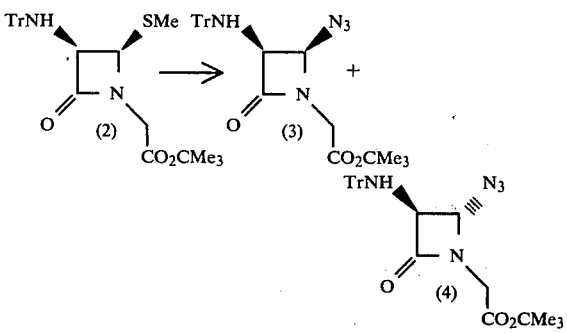

The lactam [(2); 8.48 g] was dissolved in dry carbon tetrachloride (500 ml) and the solution cooled to −20°. Chlorine (1.23 g) in dry carbon tetrachloride (50 ml) was added dropwise over 1 h., and then the solution was allowed to warm to 0°. The solvent was evaporated, the residue dissolved in carbon tetrachloride (100 ml) and the solvent re-evaporated. The product was dried (2 mm/2 h.) and then dissolved in dry dimethylformamide (400 ml). Powdered sodium azide (2.27 g) was added, the mixture stirred at room temperature for 18 h., and then poured into ethyl acetate/water. The organic layer was separated, washed with brine (×2), dried and evaporated. Chromatography on sicilca gave the cis-isomer [3; 6.11 g]. m.p. 142°–143° (ethyl acetate/petroleum other) $[\alpha]_D^{23} = +20.3$ (c=1 in chloroform) νmax (CHCl$_3$) 2100, 1770, 1735 cm$^{-1}$. δppm (CDCl$_3$) 1.45 (9H, s), 2.93 (1H, d, J 11 Hz, exch.), 3.57 and 4.22 (2H, ABq, J 18 Hz), 4.40–4.77 (2H, m, becomes 2H, s, at 3.95 exch.), 7.3–8.0 (15H, m). (Found: C, 69.7; H, 6.0; N, 14.5; C$_{28}$H$_{29}$N$_5$O$_3$ requires C, 69.6; H, 6.0; N, 14.5%).

Further elution gave the trans-isomer [4; 2.2 g], m.p. 135° (ethyl acetate/petroleum ether) $[\alpha]_D^{23} = -52.8°$ (c=1.1 in chloroform) νmax (CHCl$_3$) 2075, 1770, 1735 cm$^{-1}$. δppm (CDCl$_3$) 1.46 (9H, s), 2.90 (1H, d, J 10 Hz exch.), 3.53 and 4.18 (2H, ABq, J 19 Hz), 4.13 (1H, s), 4.35 (1H, s), 7.1–7.8 (15H, m). (Found: C, 69.5; H, 6.1; N, 14.5; C$_{28}$H$_{29}$N$_5$O$_3$ requires C, 69.6; H, 6.0; N, 14.5%).

EXAMPLE 3

(3S,4R)-4-Azido-1-(1-t-butoxycarbonyl-but-3-ynyl)-3-triphenylmethylaminoazetidin-2-one (5)

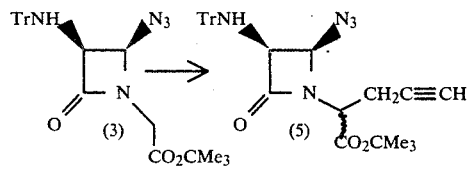

To a stirred solution of hexamethyldisilazane (177 mg) in dry tetrahydrofuran (2 ml) under argon at 0°, was added dropwise, n-butyl lithium (0.44 ml; 2.5 M solution in hexane). After 10 min. the solution was cooled to −76° and the lactam [(3); 483 mg] in dry tetrahydrofuran (5 ml) added over 5 min. After a further 10 min. a solution of propargyl bromide (600 mg) in dry tetrahydrofuran (3 ml) was added dropwise over 5 min. The reaction mixture was stirred for a further 15 min. and was then poured into ethyl acetate/very dilute hydrochloric acid. The organic layer was separated, washed with brine (×2), dried and evaporated. Chromatography on silica afforded the product [(5); 350 mg]. νmax. (CHCl$_3$) 3270, 2100, 1770, 1735 cm$^{-1}$. The nmr spectrum was complex but indicated that the product was a mixture of epimers.

EXAMPLE 4

(3aR,4S) t-Butyl 4,5,7,8-tetrahydro-5-oxo-4-triphenylmethylamino-3aH-azeto-[1,2-a]v-triazolo[3,4-c]pyrimidine-7-carboxylate (6)

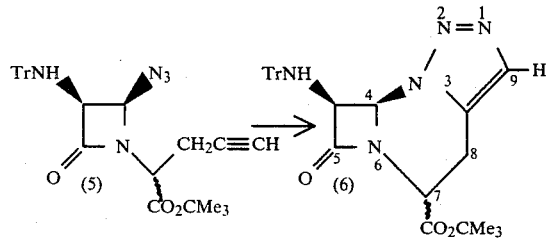

The lactam [(5); 1.28 g] was refluxed in dry toluene (750 ml) for 8 h. The solvent was evaporated and the residue chromatographed on silica to give two C-7 isomers of (6) as amorphous solids. Less polar isomer (tlc) (61%) $[\alpha]_D^{23} = -31°$ (c=1.09 in chloroform) νmax. 3315, 1783, 1738 cm$^{-1}$. δppm (CDCl$_3$) 1.32 (9H, s), 2.40 b (1H, s, exch.), 3.21 (1H, d, J 4 Hz), 4.5–4.75 (2H, m) 5.78 (1H, d, J 4 Hz), 7.1–7.7 (16H, m). (Found: C, 71.4; H, 6.1; N, 13.3; C$_{31}$H$_{31}$N$_5$O$_3$ requires C, 71.4; H, 6.0; N, 13.4%). More polar isomer (25%) $[\alpha]_D^{23} = -15°$ (c=1.13 in chloroform). νmax 3300, 1788, 1740 cm$^{-1}$. δppm (CDCl$_3$) 1.49 (9H, s), 2.3 g (1H, s, exch.), 3.03–3.48 (2H, m), 3.56–3.8 (1H, m), 4.63 b (1H, s, becomes d, J 4 Hz on exch.), 5.38 (1H, d, J 4 Hz), 7.0–7.55 (16H, m). (Found: C, 71.9; H, 6.0; N, 13.3; C$_{31}$H$_{31}$N$_5$O$_3$ requires C, 71.4; H, 6.0; N, 13.4%).

EXAMPLE 5

(3aR,4S) t-Butyl 4,5-dihydro-5-oxo-4-triphenylmethylamino-3aH-azeto-[1.2-a]v-triazolo[3,4-c]pyrimidine-7-carboxylate (8)

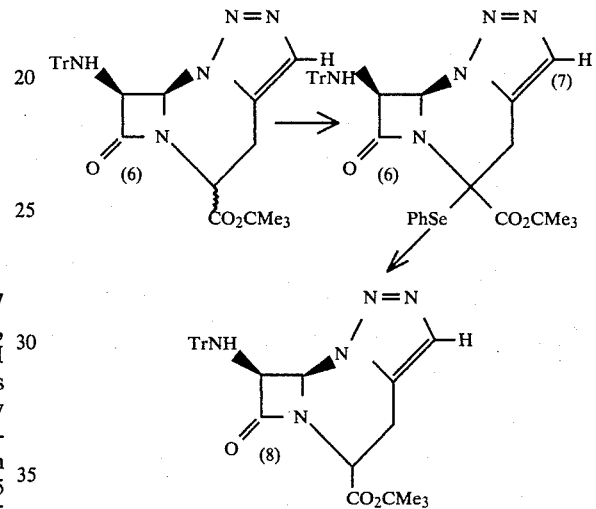

Hexamethyldisilazane (177 mg) in dry tetrahydrofuran (3 ml) was cooled to 0° under argon, and n-butyl lithium (0.44 ml of 2.5 M in hexane) added. After 10 min. the stirred solution was cooled to −76° and a solution of the β-lactam [(6); 521 mg, mixed isomers] in dry tetrahydrofuran (5 ml) was added dropwise over 10 min. After a further 10 min. phenylselenenyl bromide in dry tetrahydrofuran [0.8 ml of a solution freshly prepared by addition of bromine (0.162 ml) to diphenyl diselenide (0.94 g) in tetrahydrofuran (4 ml)] was added dropwise over 5 min. The solution was poured into ethyl acetate/brine and the organic layer separated, washed successively with dilute aqueous sodium bicarbonate and brine, dried and evaporated. Filtration through a short silica column gave the seleneno-triazole [(7); 448 mg] νmax (CHCl$_3$) 3360, 1795, 1725 cm$^{-1}$.

The product [(7); 448 mg] was dissolved in ethyl acetate (10 ml) at 0° and m-chloroperbenzoic acid (226 mg) added portionwise over 2 min. The solution was allowed to warm to room temperature and was then washed successively with aqueous sodium bicarbonate and brine, dried and evaporated. Chromatography on silica afforded the triazole [(8); 265 mg] $[\alpha]_D^{23} = +1.12°$ (c=1 in chloroform). νmax (CHCl$_3$) 3360, 1806, 1720, 1620 cm$^{-1}$. δppm (CDCl$_3$) 1.51 (9H, s), 3.24 b (1H, s, exch), 5.09 b (2H, s, becomes sharp 2H, s, on exch.), 7.0–7.7 (16H, m), 7.78 (1H, s); λmax. (EtOH) 309 nm (ε=8,700). (Found: C, 72.0; H, 5.9; N, 13.4. C$_{31}$H$_{29}$N$_5$O$_3$ requires C, 71.7; H, 5.6; N, 13.5%).

EXAMPLE 6

(3aR,4S) t-Butyl 4,5-dihydro-5-oxo-4-phenoxyacetamido-3aH-azeto-[1,2-a]v-triazolo[3,4-c]pyrimidine-7-carboxylate (10)

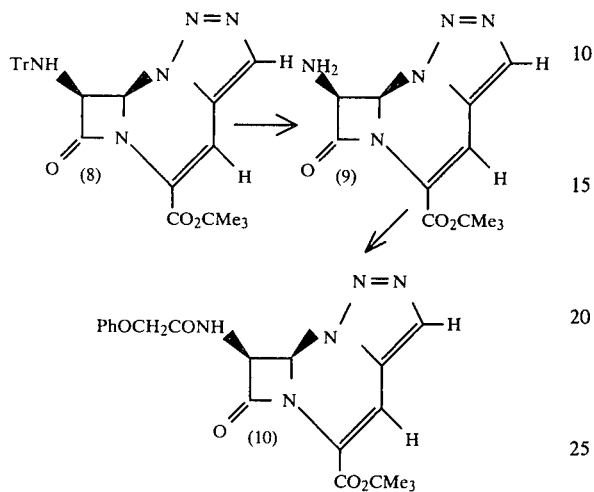

The lactam [(8); 100 mg.] was dissolved in dry methylene dichloride (3 ml) at −20° and toluene-p-sulphonic acid (40 mg) added dropwise in the minimum volume of methanol (0.5 ml). After 2¼ h. at +5° the solvents were evaporated and the residue dried in vacuo.

The crude toluene-p-sulphonic acid salt of the free base (9) was dissolved in dry methylene chloride at −20° and triethylamine (80 mg) added in methylene chloride (0.5 ml), followed by phenoxyacetyl chloride (64 mg) in methylene chloride (1 ml). The reaction mixture was allowed to warm to ambient temperature and was then washed successively with aqueous sodium bicarbonate and brine (×2), dried and evaporated. Chromatography on silica gave the acylamino-derivative (10) as a white solid (71 mg) by trituration of the purified product with ether. νmax. (Nujol) 3315, 1805, 1718, 1680, 1625 cm⁻¹. δppm (CDCl₃) 1.55 (9H, s), 4.37 (2H, s), 5.78 (1H, dd, J 4 Hz and 8 Hz). 5.89 (1H, d, J 4 Hz), 6.7–7.5 (7H, m), 7.77 (1H, s) λmax (EtOH) 313 nm (ε=9,600).

EXAMPLE 7

(3aR,4S)4,5-dihydro-5-oxo-4-phenoxyacetamido-3aH-azeto-[1,2-a]v-triazolo[3,4-c]pyrimidine-7-carboxylic acid (11)

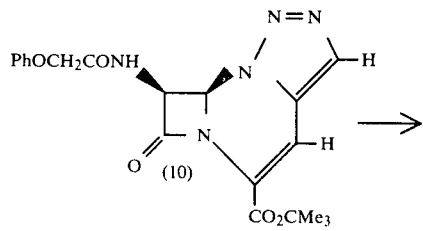

-continued

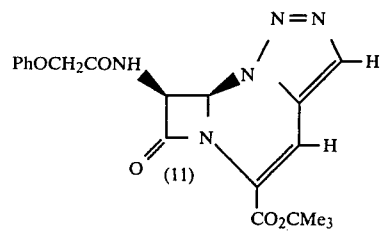

The ester [(10); 47 mg] was dissolved in trifluoroacetic acid (2 ml) and the pale yellow solution left at room temperature for 35 min. The solvent was evaporated off, the residue treated with toluene, and the mixture evaporated; this procedure was repeated. Trituration with ether gave the free acid (11) as a white amorphous solid (36 mg). νmax. (Nujol) 3350 b, 1810, 1720sh, 1690, 1623 cm⁻¹. δppm (CDCl₃+2 drops (CD₃)₂SO) 4.43 (2H, s), 5.2–5.7 b (1H, s, exch.), 5.95 (2H, m. collapses to two d's at 5.91 and 6.03, both J 4 Hz, on exch.), 6.8–7.6 (6H, m), 7.88 (1H, s), 8.55 (1H, d, J 8 Hz, exch.). λmax. (EtOH) 327 nm (ε6,500).

The minimum inhibitory concentrations (MIC) of this compound required to inhibit the growth of various bacteria on nutrient agar are tabulated below:

| Gram-positive bacteria | MIC (μg/ml) |
| --- | --- |
| B. subtilis | 2.5 |
| Staph. aureus Oxford | 10 |
| Staph. aureus Russell* | 50 |
| β-Haemolytic Strep CN10 | 10 |

*β-Lactamase-producing strain

EXAMPLE 8

(3S,4R)-4-Azido-1-(1-t-butoxycarbonyl-4-phenyl-but-3-vnyl)-3-triphenyl-methylaminoazetidin-2-one (12)

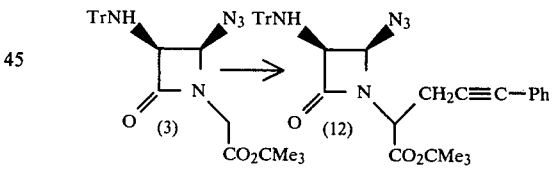

The lactam [(3); 3.59 g] was dissolved in tetrahydrofuran (100 ml) and the solution cooled to −76° under argon. Lithium hexamethyldisilazide in tetrahydrofuran [15 ml of a solution prepared by addition of n-butyl lithium (6.55 ml; 2.5 M solution in hexane) to hexamethyldisilazane (2.63 g) in tetrahydrofuran (20 ml)] was added dropwise over 20 min. After a further 45 min. 3-phenyl-prop-2-ynyl bromide (1.6 g) in tetrahydrofuran (5 ml) was added dropwise over 10 min. The solution was stirred at −76° for 45 min. and then poured into ethyl acetate/water. The organic layer was separated, washed with brine, dried and evaporated. Chromatography on silica gave the product (12) as an amorphous solid (3.1 g) [α]$_D^{25.5}$ = −25.6° (c=1.57 in chloroform). νmax. (CHCl₃) 2125, 1770, 1740 cm⁻¹. δppm (CDCl₃) 1.41 (9H, s), 2.75–3.0 (3H, m, 1H exch.), 4.35–4.8 (3H, m), 6.9–7.8 (20H, m).

EXAMPLE 9

(3aR,4S) t-Butyl 4,5,7,8-tetrahydro-5-oxo-9-phenyl-4-triphenylmethylamino-3aH-azeto-[1,2-a]triazolo[3,4-c]pyrimidine-7-carboxylate (13)

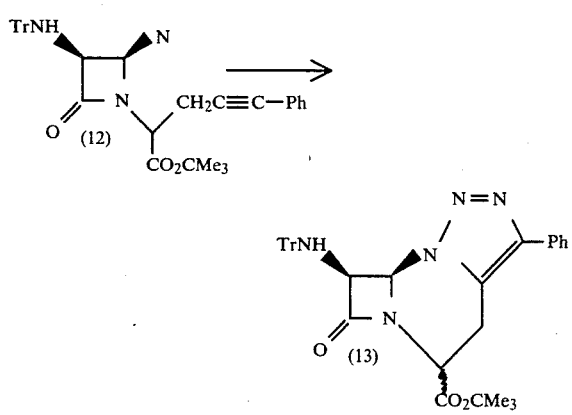

The lactam [(12); 1.5 g] was refluxed in toluene (500 ml) under argon for 5.75 h. The solvent was evaporated and the residue chromatographed on silica to give the phenyltriazole [(13); 1.374 g] $[\alpha]_D^{25.5} = -5.7°$ (c=1 in chloroform). νmax. (CHCl$_3$) 3355, 1785, 1738 cm$^{-1}$. δppm (CDCl$_3$) 1.29 (9H, s), 2.51 b (1H, s, exch.), 3.2–3.66 (2H, m), 4.68 (1H, t, J 3.5 Hz), 4.71 (1H, d, J 4 Hz), 5.72 (1H, d, J 4 Hz), 7.0–7.8 (20H, m). The product appeared to be a single C-7 isomer.

EXAMPLE 10

(3aR,4S) t-Butyl 4,5-dihydro-5-oxo-9-phenyl-4-triphenylmethylamino-3aH-azeto-[1,2-a]v-triazolo[3,4-c]pyrimidine-7-carboxylate (15)

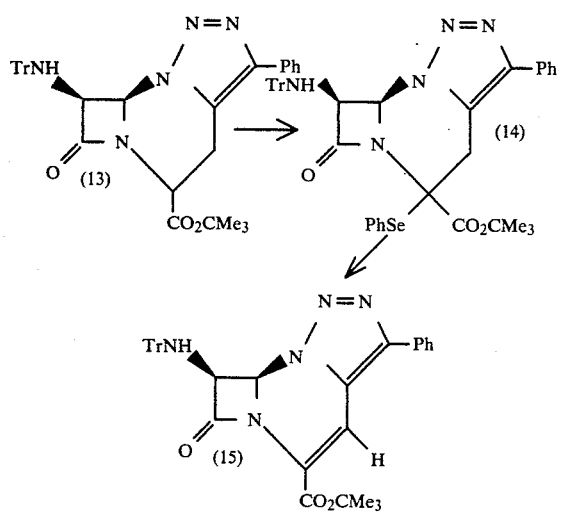

Hexamethyldisilazane (861 mg) was dissolved in tetrahydrofuran (15 ml) under argon at 0° and n-butyl lithium (2.14 ml; 2.5 M solution in hexane) added. After 10 min. the solution was cooled to −76° and the lactam [(13); 1.452 g] added dropwise in dry tetrahydrofuran (20 ml) over 10 min. After a further 10 min. phenylselenenyl bromide in dry tetrahydrofuran [7.0 ml of a solution freshly prepared by addition of bromine (0.324 ml) to diphenyl diselenide (1.88 g) in tetrahydrofuran (8 ml)] was added dropwise over 15 min. The reaction mixture was poured into ethyl acetate, the organic layer washed successively with aqueous sodium bicarbonate, water, and brine, dried and evaporated. Chromatography on silica afforded the selenide [(14); 1.44 g] νmax. (CHCl$_3$) 3350, 1792, 1722$^{-1}$. δppm (CDCl$_3$) 1.49 (9H, s), 2.47 b (1H, s, exch.). 3.0 and 3.56 (2H, ABq, J 18 Hz), 4.69 b (1H, s, becomes d J 4 Hz on exch.), 5.61 (1H, d, J 4 Hz), 6.8–7.6 (25H, m).

The ester [(14); 1.37 g] was dissolved in ethyl acetate (60 ml) at 0° and m-chloroperbenzoic acid (628 mg) added portionwise over 10 min. After 1 h. at 0° the mixture was washed successively with dilute aqueous sodium bicarbonate and brine, dried and evaporated. Silica-gel chromatography gave the required product [(15); 932 mg] $[\alpha]_D^{23} = 172.6°$ (c=1.37 in chloroform) νmax. (CHCl$_3$) 3355, 1805, 1715, 1605 cm$^{-1}$. δppm (CDCl$_3$) 1.52 (9H, s), 3.3 b (1H, s, exch.), 5.1 (2H, d, collapses to s on exch.) 6.8–7.8 (21H, m). λmax. (EtOH) 333 nm (ε17,900) (Found: C, 74.7; H, 5.8; N, 11.7. C$_{37}$H$_{33}$N$_5$O$_3$ requires C, 74.6; H, 5.5; N, 11.8%).

EXAMPLE 11

(3aR,4S) t-Butyl 4,5-dihydro-5-oxo-9-phenyl-4-D-mandelylamino-3aH-azeto-[1,2-a]v-triazolo[3,4-c]pyrimidine-7-carboxylate (17)

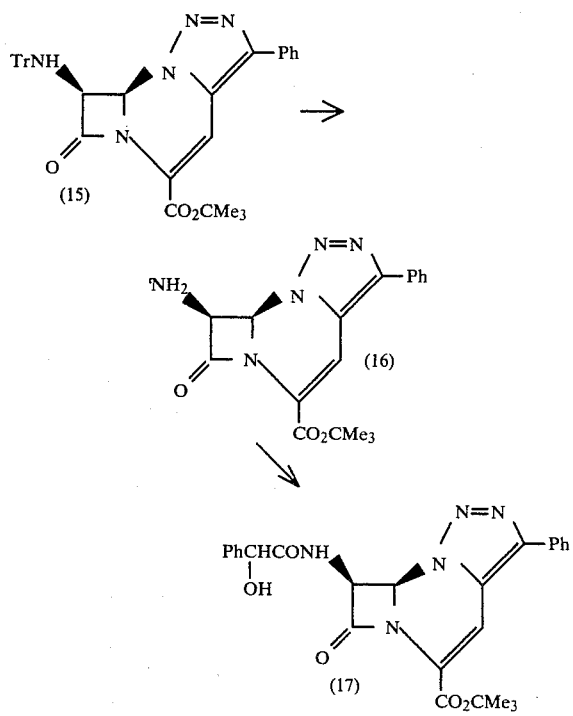

The lactam [(15); 298 mg] was dissolved in dry methylene chloride (10 ml) and the solution cooled to −20°. Toluene-p-sulphonic acid (209 mg) was added dropwise in the minimum volume of methanol and the solution allowed to warm to room temperature. After 1 hr. the solvent was evaporated and the residue dissolved in ethyl acetate. The solution was washed with dilute aqueous sodium bicarbonate, followed by brine, dried and evaporated. The free base (16), a white solid, was dried in vacuo. The total crude product (16) was dissolved in dry methylene chloride (10 ml) and the solution cooled to −20°. D-Mandelyl O-carboxyanhydride (196 mg) was added in one portion. The solvent was evaporated and the residue dissolved in ethyl acetate. The solution was washed successively with aqueous sodium bicarbonate, water, and brine, dried and evaporated. Chromatography on silica gave the acylaminoderivative [(17); 208 mg] $[\alpha]_D^{23} = +63.85°$ (c=1, in chloroform). νmax. 3380, 3300 b, 1810, 1712, 1690sh cm$^{-1}$. δppm (CDCl$_3$) 1.57 (9H, s), 5.35 (1H, s), 5.88 (1H, d, J 4 Hz), 6.03 (1H, dd, J 4 Hz and 9 Hz), 7.0–7.5 (11H, m), 8.02 (1H, d, J 9 Hz). λmax. (EtOH) 337 nm (ε12,800).

EXAMPLE 12

(3aR,4S) 4,5-Dihydro-5-oxo-9-phenyl-4-D-mandelylamino-3aH-azeto-[1,2a]v-triazolo[3,4-c]pyrimidine-7-carboxylic acid (18)

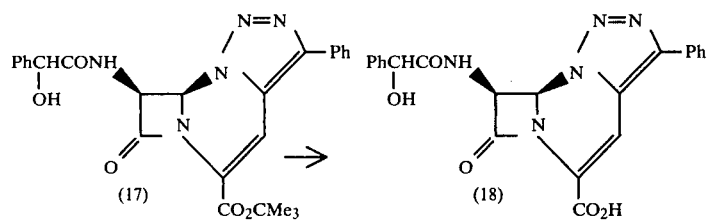

The ester [(17); 100 mg] was dissolved in trifluoroacetic acid (2 ml). After 30 min. at room temperature the solvent was evaporated off, the residue treated with toluene, and the mixture evaporated; this procedure was repeated. Trituration with ether gave the free acid (18) as a white amorphous solid (82 mg). $[\alpha]_D^{22} = 109°$ (c=0.76 in aqueous sodium bicarbonate) νmax (KBr) 3400 b, 1790, 1720, 1670 cm$^{-1}$. δppm (D$_6$DMSO) 4.86 (1H, s), 5.0 b (2H, s, exch.), 5.85 (1H, dd, J 4 Hz and 9 Hz), 6.1 (1H, d, J 4Hz), 7.0–7.8 (11H, m), 8.91 (1H, d, J 9 Hz). λmax [80% EtOH+20% (0.3% w/w sodium bicarbonate)] 266 nm (ε9,700 ), 404 (68 5,570).

The minimum inhibitory concentrations (MIC) of this compound required to inhibit the growth of various bacteria in nutrient broth are tabulated below. (10$^{-4}$ dilution).

| Gram-positive bacteria | MIC (μg/ml) |
|---|---|
| *Staph. aureus* Oxford | 31 |
| *Staph. aureus* Russell* | 125 |
| Gram-negative bacteria | MIC (μg/ml) |
| *E. coli* JT 1 | 125 |
| *E. coli* NCTC 10418 | 125 |

*β-Lactamase producing strains

EXAMPLE 13

(3S,4R)-4-Azido-1-(1-t-butoxycarbonyl-1-phenylselenenyl-4-phenyl-but-3-ynyl)-3-triphenylmethylaminoazetidin-2-one (19)

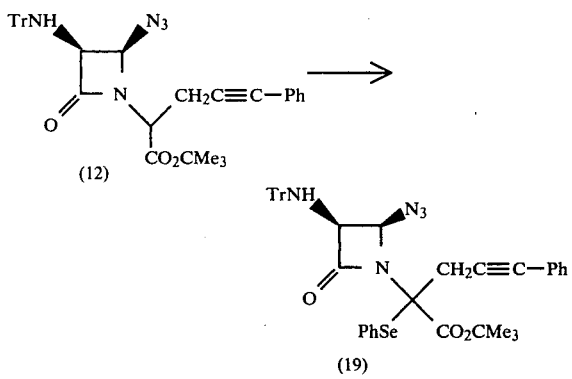

Hexamethyldisilazane (624 mg) in tetrahydrofuran (5 ml) was cooled to 0° under argon and n-butyl lithium (1.56 ml; 2.5 M solution in hexane) added. After 15 min. the solution was cooled to −76° and the lactam [(12); 1.41 g] in tetrahyrofuran (20 ml) added dropwise over 15 min. After 10 min phenylselenenyl bromide in tetrahydrofuran [3.1 ml of solution prepared by adding bromine (0.162 g) to diphenyl diselenide (0.94 g) in tetrahydrofuran (5 ml)] was added over 5 min. The reaction mixture was poured into ethyl acetate/water, the organic layer separated, washed with brine (×2), dried, and evaporated. Silica gel chromatography gave [(19); 1.48 g] νmax. (CHCl$_3$) 3340, 2125, 1765, 1730 cm$^{-1}$. δppm (major isomer) (ca 85%) 1.48 (9H, s), 2.72 b (1H, s, exch.), 3.07 and 3.89 (2H, ABq, J 16 Hz) 3.43 b (1H, s, becomes d J 4 Hz on exch), 4.19 (1H, d, J 4 Hz), 6.8–7.6 (25H, m). A singlet at 1.38δ was probably due to the —CO$_2$CMe$_3$ of the minor isomer. A doublet (J 4 Hz) at 4.67δ being one of the β-lactam protons of the minor isomer.

EXAMPLE 14

(3S,4R)-4-Azido-1-(-1-t-butoxycarbonyl-1-phenylselenenyl-4-phenyl-but-3-ynyl)-3-(N-t-butoxycarbonyl-D-α-phenylglycyl)aminoazetidin-2-one (21)

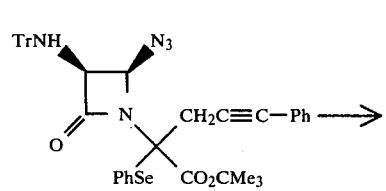

-continued

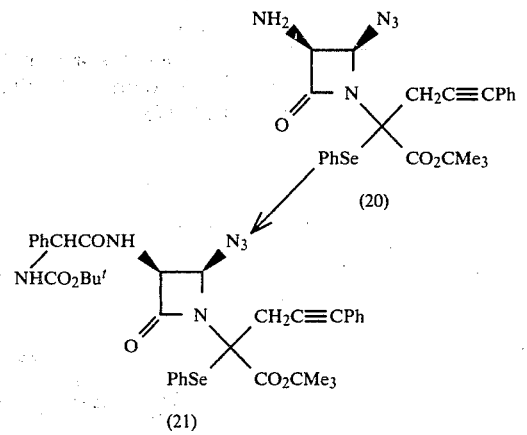

The lactam [(19); 753 mg] was dissolved in methylene chloride (10 ml) at −20° and toluene-p-sulphonic acid (209 mg) in the minimum volume of methanol added dropwise over 2 min. The reaction mixture was kept at −5° for 16h and then at +3° for 3 h. The solvents were evaporated off and the residue dissolved in ethyl acetate. The solution was washed successively with dilute aqueous sodium bicarbonate and brine (×2), dried and evaporated. The residual gum (20) was dried in vacuo.

Methyl chloroformate (104 mg) in dry tetrahydrofuran (6 ml) was cooled to −20°. To this solution was added, dropwise with stirring, a solution of N-(t-butoxycarbonyl)-D-α-phenylglycine (276 mg), triethylamine (112 mg), and N,N-dimethylbenzylamine (1 drop) in tetrahydrofuran (10 ml) over 5 min. After a further 30 min at −20° the crude free base (20) was added dropwise over 5–10 min in dry tetrahydrofuran (10 ml). After stirring for a further 1 h. the mixture poured into ethyl acetate/water. The organic layer was separated, washed successively with very dilute hydrochloric acid and brine (×2) dried and evaporated. Chromatography on silica provided the product [(21); 500 mg]. νmax. 3440, 2135, 1780, 1710 b cm$^{-1}$.

EXAMPLE 15

(3aR,4S) t-Butyl 4,5-dihydro-5-oxo-9-phenyl-4-(N-t-butoxycarbonyl-D-α-phenylglycyl)amino-3aH-azeto[1,2-a]v-triazolo[3,4-c]pyrimidine-7-carboxylate (23)

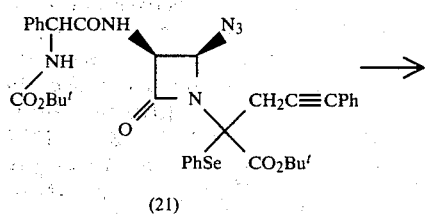

-continued

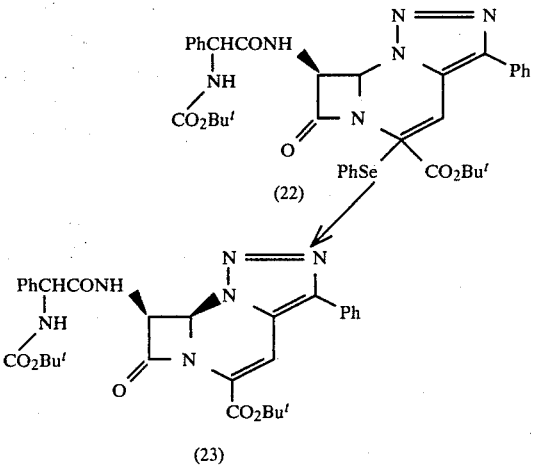

The lactam [(21); 457 mg] was refluxed in dry toluene (175 ml) under argon for 11½ h. The solvent was evaporated and the residue (22) dissolved in ethyl acetate and the solution cooled to 0°. m-Chloroperbenzoic acid (212 mg) was added in portions over 1–2 min and the mixture allowed to warm to room temperature. The solution was washed successively with aqueous sodium bicarbonate and brine (×2), dried and evaporated. Chromatography on silica afforded the required product [(23); 251 mg] [α]$_D^{23}$ = +44.63° (c=1 in chloroform) νmax (CHCl$_3$) 3380, 3270, 1808, 1710 b cm$^{-1}$. δppm (CDCl$_3$) 1.3 (9H, s), 1.54 (9H, s), 4.55 (1H, s, exch.), 5.35 (1H, m, becomes s on exch), 5.67 (1H, dd, J 9 Hz, 4 Hz), 5.87 (1H, d, J 4 Hz), 7.0–8.0 (12H, m) λmax (EtOH) 337 nm (ε 12,900), 254 nm (ε 8,100).

EXAMPLE 16

(3aR,4S)-4,5-Dihydro-5-oxo-9-phenyl-4-D-α-phenylglycylamino-3aH-azeto[1,2-a]v-triazolo[3,4-c]pyrimidine-7-carboxylic acid, trifluoroacetic acid salt (24)

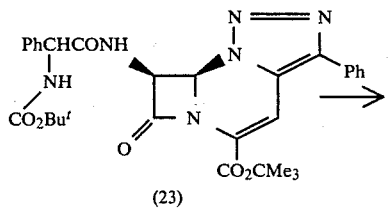

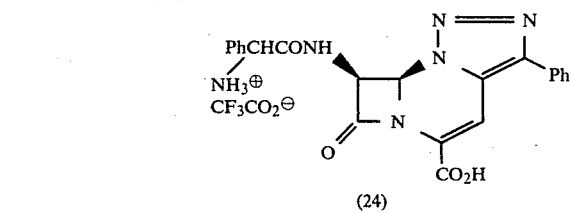

The lactam (95 mg) was dissolved in trifluoroacetic acid (2 ml). After 30 min at room temperature the solvent was evaporated off, the residue treated with toluene, and the mixture evaporated; this procedure was repeated. Trituration with ether gave the TFA salt [(24); 69 mg] [α]$_D^{22}$ +43.6° (c=0.32 in DMSO) νmax (KBr) 3400 b, 3050 b, 1795, 1670 b cm$^{-1}$. δppm (D$_6$-DMSO) 3.0–5.0 b (4H, s, exch.), 4.94 (1H, s), 6.1 (2H, m becomes 2 d's at 5.85 and 6.12, both J 4 Hz, on exch.), 7.1-7.8 (11H, m), 9.25 (1H, d, J 9 Hz, exch). λmax (EtOH) 327 nm (ε 12,000), 260 nm (ε 9,200).

The minimum inhibitory concentrations (MIC) of this compound required to inhibit the growth of various bacteria in nutrient broth are tabulated below: ($10^{-4}$ dilution).

| Gram-positive bacteria | MIC (μg/ml) |
|---|---|
| Staph aureus Oxford | 62 |
| Staph aureus Russell* | 125 |
| Gram-negative bacteria | MIC (μg/ml) |
| E. coli JT1 | 125 |
| E. coli NCTC 10418 | 125 |

*β-Lactamase producing strain

EXAMPLE 17

(3S,4R)-4-Azido-1-Z(1-t-butoxycarbonyl-4-phenyl-but-1-en-3-ynyl)-3-triphenylmethylaminoazetidin-2-one (25)

(3S,4R,)-4-Azido-1-E(1-t-butoxycarbonyl-4-phenyl-but-1-en-3-ynyl)-3-triphenylmethylaminoazetidin-2-one (26)

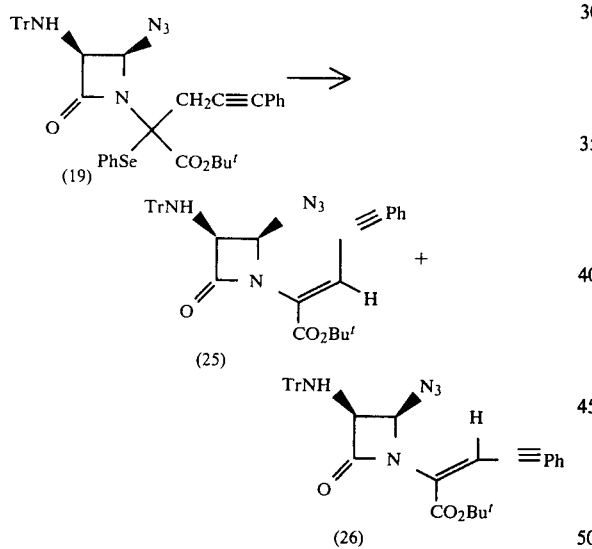

The lactam [(19); 570 mg] was dissolved in ethyl acetate (30 ml) at 0° and m-chloroperbenzoic acid (260 mg) added in portions over 5 min. The mixture was washed successively with aqueous sodium bicarbonate, brine, dried, and evaporated. Chromatography gave the two isomers of the ene-yne.

Major (Z)-isomer (25) (60%). νmax ($CHCl_3$) 3340, 2205, 2125, 1785, 1715, 1608 $cm^{-1}$ δppm ($CDCl_3$) 1.48 (9H, s), 2.96 b (1H, s, exch.), 4.47 b (1H, s, becomes d, J 4 Hz on exch.), 4.95 (1H, d, J 4 Hz), 6.49 (1H, s), 7.0-7.6 (20H m). Minor (E)-isomer (26) (20%) νmax 3350, 2190 (w), 2150, 1770, 1710 $cm^{-1}$. δppm ($CDCl_3$) 1.48 (9H, s), 2.95 b (1H, s, exch.), 4.45 b (1H, s, becomes d, J 4 Hz, on exch.), 4.96 (1H, d, J 4 Hz), 7.02 (1H, s), 7.1-7.6 (20H, m).

EXAMPLE 18

(3aR,4S) t-Butyl-4,5-dihydro-5-oxo-9-phenyl-4-triphenylmethylamino-3aH-azeto[1,2-a]v-triazolo[3,4-c]pyrimidine-7-carboxylate (15)

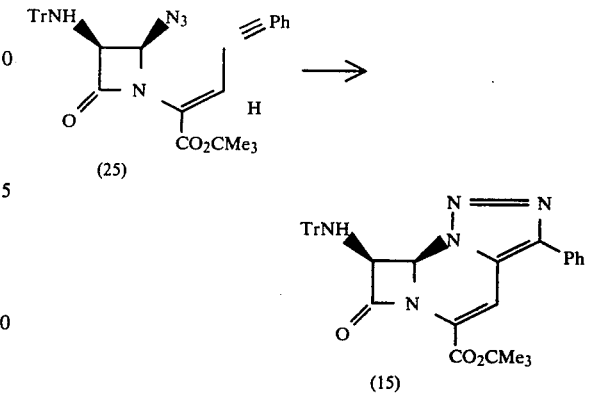

The Z-isomer [(25); 245 mg] was refluxed under argon in toluene (120 ml) for 4 h. The solvent was evaporated and the residue chromatographed on silica to give the product [(15); 219 mg], identical in all respects to that prepared in Example 10.

The lactam [(26); 70 mg] slowly decomposed when refluxed under argon in toluene (40 ml).

EXAMPLE 19

(3S,4R)-4-Azido-1-(1-t-butoxycarbonyl-4-p-nitrophenyl-but-3-ynyl)-3-triphenylmethylaminoazetidin-2-one (27)

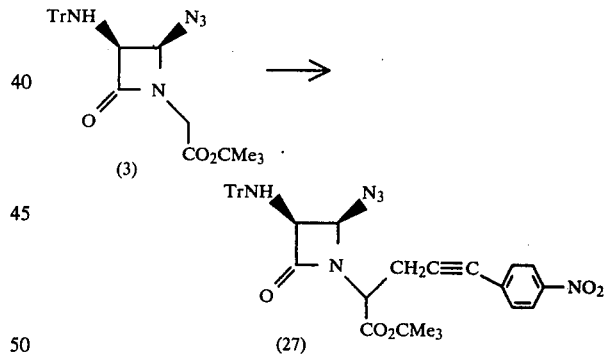

Hexamethyldisilazane (975 mg) was dissolved in dry tetrahydrofuran (20 ml) at 0° under argon, and n-butyl lithium (2.42 ml; 2.5 M solution in hexane) added. The solution was cooled to −76° after 10 min. and the lactam [(3); 2.6 g] added dropwise in dry tetrahydrofuran (40 ml) over 15 min. After a further 10 min 3-p-nitrophenyl-prop-2-ynyl bromide (1.454 g) in dry tetrahydrofuran (10 ml) was added dropwise over 10 min. After 1 h at −76° the mixture was poured into ethyl acetate/very dilute hydrochloric acid. The organic layer was separated, washed with brine (×2), dried, and evaporated. Chromatography on silica afforded the acetylenic lactam [(27); 1.004 g] $[α]_D^{23} = -19.96°$ (c=1.05 in chloroform) νmax ($CHCl_3$) 2125, 1775, 1740, 1600, 1520, 1345 $cm^{-1}$. δppm ($CDCl_3$) 1.42 (9H, s), 2.75-3.15 (3H, m becomes 2H, d, at 2.95 J 6 Hz on exch.), 4.3-4.85 (3H, m), 7.05-8.35 (19H, m).

EXAMPLE 20

(3aR,4S) t-Butyl 4,5,7,8-tetrahydro-5-oxo-9-p-nitrophenyl-4-triphenylmethylamino-3aH-azeto[1,2-a]v-triazolo[3,4-c]pyrimidine-7-carboxylate (28)

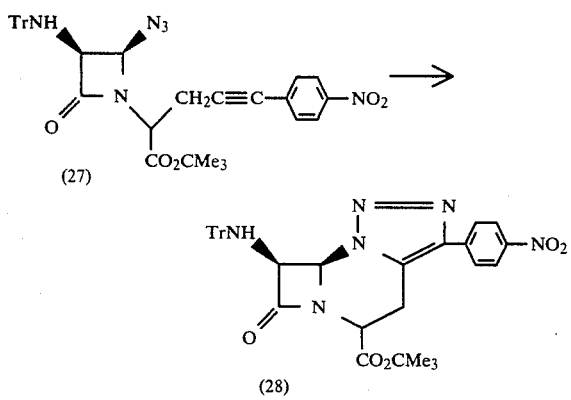

The lactam [(27); 1.2 g] was refluxed under argon in toluene (600 ml) for 7 h. The solvent was evaporated and the residue chromatographed on silica to give the triazole [(28); 1.08 g]. $[\alpha]_D^{23} = +33.96°$ (c=1.03 in chloroform). νmax (CHCl$_3$) 1790, 1740, 1600, 1520, 1345 cm$^{-1}$. δppm (CDCl$_3$) 1.29 (9H, s), 2.45 (1H, d, J 9 Hz exch.), 3.35–3.55 (2H, m), 4.65–4.9 (2H, m), 5.73 (1H, d, J 4 Hz), 7.0–7.6 (15H, m), 7.84 and 8.25 (4H, ABq, J 9 Hz).

EXAMPLE 21

(3aR,4S) t-Butyl 4,5-dihydro-5-oxo-9-p-nitrophenyl-4-triphenylmethylamino-3aH-azeto[1,2-a]v-triazolo[3,4-c]pyrimidine-7-carboxylate (30)

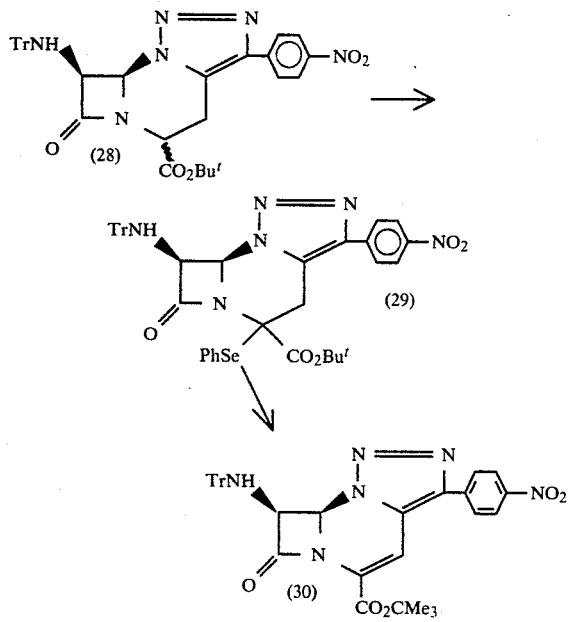

Hexamethyldisilazane (276 mg) was dissolved in dry tetrahydrofuran (3 ml) under argon at 0° and n-butyl lithium (0.68 ml; 2.5 M solution in hexane) added. The solution was cooled to −76° after 10 min and the lactam [(28); 1.0 g] in tetrahydrofuran (8 ml) added dropwise over 5 min. After 10 min phenylselenenyl bromide in tetrahydrofuran [1.25 ml of a solution prepared by addition of bromine (0.162 ml) to diphenyl diselenide (0.94 g) in tetrahydrofuran (4 ml)] was added dropwise over 3–4 min. The mixture was poured into ethyl acetate/very dilute hydrochloric acid and the organic layer separated, washed with brine, dried and evaporated. Filtration through a silica column provided the selenide [(29); 750 mg]. The latter was dissolved in ethyl acetate (50 ml) at 0° and m-chloroperbenzoic acid (330 mg) added portionwise over 5 min. The reaction mixture was allowed to warm to room temperature and was then washed successively with dilute aqueous sodium bicarbonate, brine, dried, and evaporated. Chromatography afforded the required product [(30); 473 mg]. m.p. 205°–208° (ethyl acetate/petrol) $[\alpha]_D^{23} = 215.4°$ (c=1 in chloroform) νmax (CHCl$_3$) 1810, 1720, 1600, 1520, 1345 cm$^{-1}$. δppm (CDCl$_3$) 1.56 (9H, s), 3.30 (1H, d, J 9 Hz exch.), 5.1–5.4 (2H, m, collapses to s 5.24 on exch.), 7.1–7.8 (16H, m), 7.96 and 8.38 (4H, ABq, J 9 Hz) λmax (EtOH) 344 nm (ε 18,100), 290 nm (ε 9,200) (Found: C, 69.2; H, 5.0; N, 13.0. C$_{37}$H$_{32}$N$_6$O$_5$ requires C, 69.4; H, 5.0; N, 13.1%).

EXAMPLE 22

(3aR,4S) t-Butyl 4,5-dihydro-5-oxo-9-p-nitrophenyl-4-phenoxyacetamido-3aH-azeto[1.2-a]v-triazolo[3,4-c]pyrimidine-7-carboxylate (32)

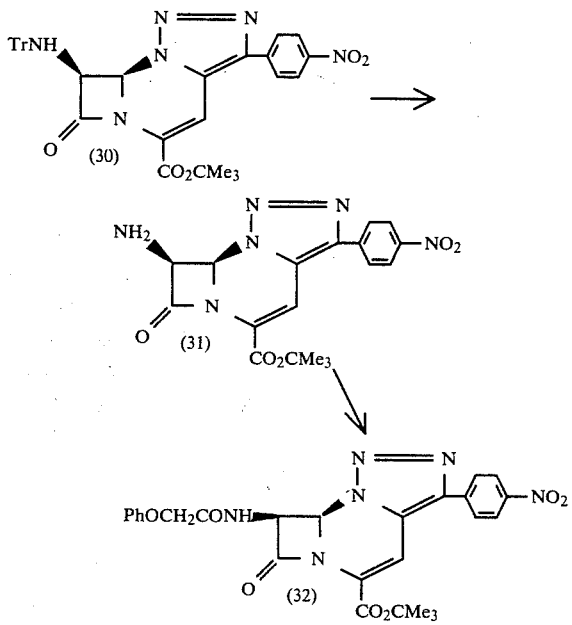

The lactam [(30); 320 mg] was dissolved in dry methylene chloride (4 ml) at −20° and toluene-p-sulphonic acid (104 mg) added dropwise in the minimum volume of methanol. The reaction mixture was allowed to warm to room temperature and after 1 h. the solvents were evaporated off. The residue was dissolved in ethyl acetate and the solution was washed successively with aqueous sodium bicarbonate and brine, dried and evaporated. The crude free base (31) was dried in vacuo and then dissolved in methylene chloride (7 ml) at −20°. Triethylamine (56 mg) in methylene chloride (1 ml) was added, followed by a solution of phenoxyacetyl chloride in methylene chloride (1 ml). The solution was allowed to warm to room temperature and was washed with water, followed by brine, dried and evaporated. Silica gel chromatography gave the acylamino-derivative [(32); 178 mg] $[\alpha]_D^{23} = +184.2°$ (c = 1.03 in chloroform) νmax (KBr) 3350, 1810, 1700, 1520, 1345 cm$^{-1}$. δppm (D$_6$DMSO) 1.54 (9H, s), 4.38 (2H, s), 5.92 (1H, dd, J 9 Hz, 4 Hz), 6.19 (1H, d, J 4 Hz), 6.7–7.35 (5H, m), 7.4 (1H, s), 8.03 and 8.30 (4H, ABq, J 9 Hz), 9.00 (1H, d, J 9 Hz). νmax (EtOH) 346 nm (ε 18,850), 290 nm (ε 9,800).

EXAMPLE 23

(3aR,4S) 4,5-Dihydro-5-oxo-9-p-nitrophenyl-4-phenoxy-acetamido-3aH azeto[1,2-a]v-triazolo[3,4-c]pyrimidine-7-carboxylic acid (33)

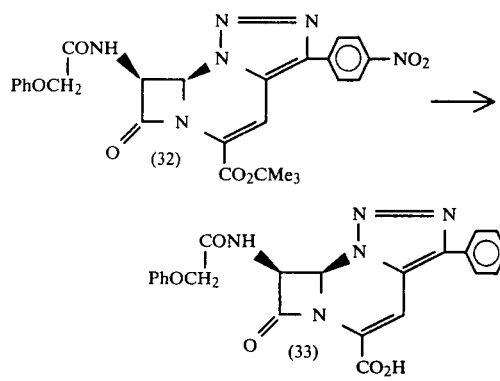

The lactam [(32); 130 mg] was dissolved in trifluoroacetic acid (4 ml). After 30 min. the solvent was evaporated off, the residue treated with toluene, and the mixture evaporated; this procedure was repeated. Trituration with ether gave the free acid (33) as a yellow solid (96 mg). $[\alpha]_D^{22} = 173.1$ (c = 1.04 in DMSO) νmax (KBr) 3380, 1800, 1700, 1600, 1530, 1345 cm$^{-1}$. δppm (D$_6$DMSO) 4.40 (2H, s), 5.8–6.05 (1H, m), 6.05–6.3 (1H, m), 6.7–7.6 (7H, m), 7.8–8.5 (4H, m), 9.01 (1H, d, J 9 Hz).

The minimum inhibitory concentrations (MIC) of this compound required to inhibit the growth of various bacteria in nutrient broth are tabulated below:

| Gram-negative bacteria | MIC (μg/ml$^{-1}$) |
|---|---|
| E. coli JT 1 | 500 |
| E. coli NCTC 10418 | 500 |

| Gram positive bacteria | MIC (μg/ml$^{-1}$) |
|---|---|
| Staph. aureus Oxford | 16 |
| Staph. aureus Russell* | 31 |

*β-lactamase producing strain

EXAMPLE 24

(3S,4R)-4-Azido-1-(-1-t-butoxycarbonyl-2-hydroxy-2-methyl-but-3-ynyl)-3-triphenylmethylaminoazetidin-2-one (34)

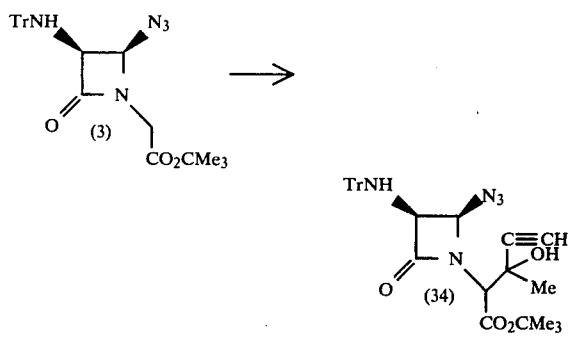

Hexamethyldisilazane (0.88 g) was dissolved in dry tetrahydrofuran at 0° under argon and n-butyl lithium (2.2 ml; 2.5 M solution in hexane) added. The solution was stirred for 10 min. and then cooled to −76° and the lactam [(3); 2.42 g] in tetrahydrofuran (30 ml) added dropwise over 20–25 min. A further 20 min. later 3-butyn-2-one (400 mg) in tetrahydrofuran (10 ml) was added dropwise over 10 min. The reaction mixture was poured into ethyl acetate/very dilute hydrochloric acid and the organic layer separated. The latter was washed with brine (×2), dried and evaporated. Chromatography gave the amorphous product [(34); 2.325 g]. νmax 3500, 3310, 1770, 1730 cm$^{-1}$. (Found: C, 69.3; H, 5.9; N, 12.3. C$_{32}$H$_{33}$N$_5$O$_4$ requires C, 69.7; H, 6.0; N, 12.7%).

EXAMPLE 25

(3aR,4S) t-Butyl 4,5-dihydro-5-oxo-7H-8-hydroxy-8-methyl-4-triphenylmethylamino-3aH-azeto[1,2-a]v-triazolo[3,4-c]pyrimidine-7-carboxylate (35)

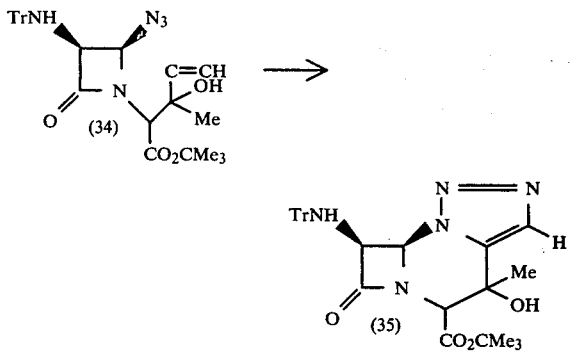

The lactam [(34); 2.265 g] was refluxed, under argon, in dry toluene (300 ml) for 2 h. The solvent was evaporated and the residue chromatographed on silica. Recrystallisation from benzene/petrol afforded the product [(35); 1.072 g] m.p. 165°–167° $[\alpha]_D^{20} = -36.9°$ (c = 0.78 in chloroform) νmax (CHCl$_3$) 3350, 1780, 1718 cm$^{-1}$. δppm (CDCl$_3$) 1.38 (9H, s), 1.69 (3H, s), 2.65 (1H, d, J 9 Hz exch), 3.66 (1H, s, exch), 4.45 (1H, s), 4.77 (1H, dd, J 4 Hz and 9 Hz, collapses to d J 4 Hz on exch), 5.60 (1H, d, J 4 Hz), 7.1–7.7 (15H, m), 7.81 (1H, s). (Found: C, 69.4; H, 6.1; N, 12.6. C$_{32}$H$_{33}$N$_5$O$_4$ requires C, 69.7; H, 6.0; N, 12.7%).

EXAMPLE 26

(3aR,4S) t-Butyl, 4,5-dihydro-5-oxo-7H-8-chloro-8-methyl-4-triphenyl-methylamino-3aH azeto[1,2-a]v-triazolo[3,4-c]pyrimidine-7-carboxylate (36)

(3aR,4S) t-Butyl 4,5-dihydro-5-oxo-7H-8-methylene-4-triphenylmethyl-amino-3aH azeto[1,2-a]v-triazolo[3,4-c]pyrimidine-7-carboxylate (37)

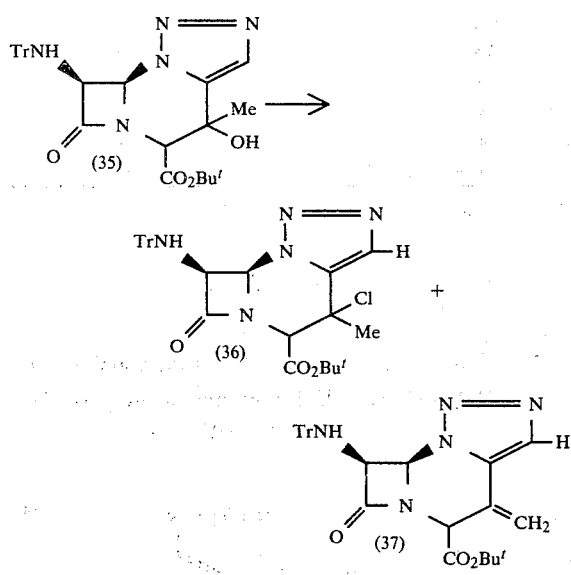

The lactam [(35); crystalline]; 1.102 g] was dissolved in dry tetrahydrofuran (50 ml) and the solution cooled to −20°. Dry lutidine (0.51 ml) was added followed by thionyl chloride (0.315 ml) dropwise in tetrahydrofuran (5 ml). After 5 min the precipitate was removed and the filtrate evaporated and redissolved in ethyl acetate. The solution was washed successively with very dilute hydrochloric acid brine (×2), dried and evaporated. The residue was chromatographed on silica to provide the chlorine [(36); 335 mg] as an amorphous solid. $[\alpha]_D^{24} = -27°$ (c=0.81 in chloroform) νmax (CHCl₃) 3350, 1788, 1735 cm⁻¹. δppm (CDCl₃) 1.4 (9H, s), 2.05 (3H, s), 2.89 (1H, d, J 9 Hz, exch), 4.57 (1H, s) 4.78 (1H, dd, J 5 Hz and 9 Hz, collapsing to d, J 5 Hz on exch.), 5.67 (1H, d, J 5 Hz), 7.1–7.7 (15H, m), 6.87 (1H, s); (Found: C, 67.7; H, 5.8; N, 11.6; Cl, 5.8. $C_{32}H_{32}N_5O_3Cl$ requires C, 67.4; H, 5.7; N, 12.3; Cl 6.2%).

Further elution of the column gave the 8-methylene derivative [(37); 475 mg] as an amorphous solid $[\alpha]_D^{24} = -22.5°$ (c=0.96 in chloroform), νmax 3350, 1790, 1735 cm⁻¹. δppm (CDCl₃) 1.42 (9H, s), 2.55 (1H, d, J 9 Hz), 4.73 (1H, dd, J 4 Hz and 9 Hz, collapsing to d J 4 Hz on exch.), 5.08 b (1H, s), 5.57 b (1H, s), 5.77 (1H, d, J 4 Hz), 5.85 b (1H, s), 7.1–7.7 (15H, m), 7.95 (1H, s). λmax (EtOH) 256 nm (ε10,300) (Found: C, 71.7; H, 6.2; N, 12.7. $C_{32}H_{31}N_5O_3$ requires C, 72.0; H, 5.9; N, 13.1%).

EXAMPLE 27

(3aR,4S) t-Butyl 4,5-dihydro-5-oxo-8-methyl-4-triphenylmethylamino-3aH-azeto[1,2-a]v-triazolo[3,4-c]pyrimidine-7-carboxylate (38)

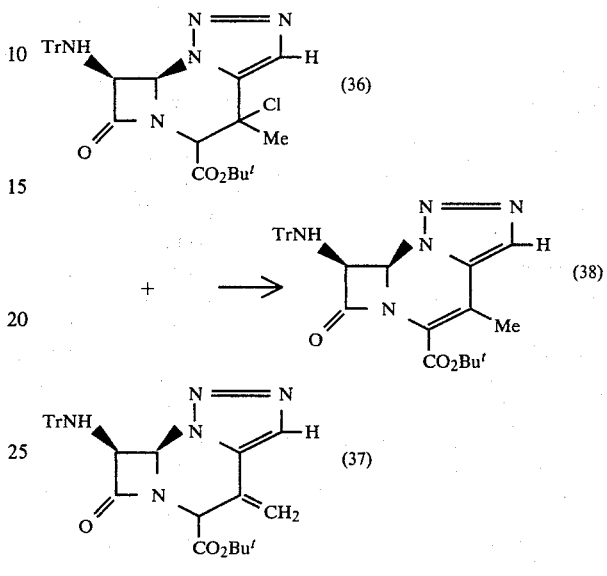

The total product from Example 26 [(36) and (37); 810 mg] was dissolved in dry methylene chloride (30 ml) at −20° and 1,5-diazabicyclo[5,4,0]undecene-5 (DBU) (200 mg) added. The reaction mixture was allowed to warm to room temperature and then the volume was reduced to ca 10 ml and the mixture filtered through a silica column, to give the product [(38); 679 mg] as a glass $[\alpha]_D^{23.5} = 2.5°$ (c=0.74 in chloroform) νmax (CHCl₃) 3350, 1800, 1709, 1600 cm⁻¹. δppm (CDCl₃) 1.5 (9H, s), 2.4 (3H, s), 3.27 (1H, d, J 10 Hz), 4.85–5.15 (2H, m, collapses to s, 5.08 on exch.), 7.1–7.8 (15H, m), 7.83 (1H, s). λmax (EtOH) 310 nm (ε9,100), 231 nm (ε18,500). (Found: C, 71.5; H, 6.2; N, 12.9. $C_{32}H_{31}N_5O_3$ requires C, 72.0; H, 5.9; N, 13.1%).

EXAMPLE 28

(3aR,4S) t-Butyl 4,5-dihydro-5-oxo-8-methyl-4-phenoxy-acetamido-3aH-azeto[1,2-a]v-triazolo[3,4-c]pyrimidine-7-carboxylate (40)

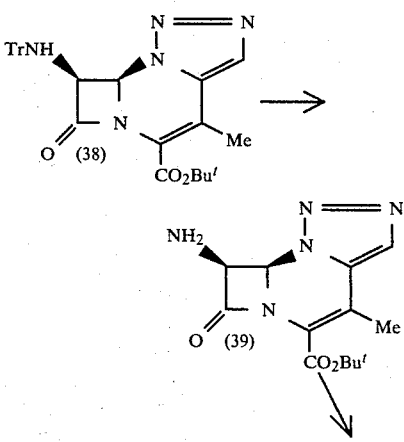

-continued

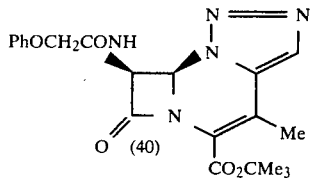

The lactam [(38); 533 mg] was dissolved in methylene chloride (10 ml) at −20° and toluene-p-sulphonic acid (210 mg) added in the minimum volume of methanol over 1-2 min. The solution was kept at 6° for 6½ hr and the solvents removed. The residue was dissolved in ethyl acetate/aqueous sodium bicarbonate. The organic layer was separated, washed with brine, dried, and evaporated to give (39). The latter was dissolved in methylene chloride (10 ml) at −20° and triethylamine (202 mg) added, followed by the dropwise addition of phenoxyacetyl chloride (190 mg) in methylene chloride (1 ml). The solution was washed with brine (×2), dried and evaporated. Chromatography on silica gave the acylamino-derivative [(40); 334 mg] as a white amorphous solid. $[\alpha]_D^{21.5} = -82.2°$ (c=1.19 in chloroform). $\nu$max (CHCl$_3$) 3425, 1805, 1700 cm$^{-1}$. $\delta$ppm (CDCl$_3$) 1.5 (9H, s), 2.48 (3H, s), 4.45 (2H, s), 5.68-6.03 (2H, m), 6.7-7.7 (6H, m), 7.88 (1H, s), $\lambda$max (EtOH) 310 nm ($\epsilon$9,500), 243 nm ($\epsilon$6,100) (Found: C, 59.3; H, 5.5; N, 16.2. C$_{21}$H$_{23}$N$_5$O$_5$ requires C, 59.3; H, 5.5; N, 16.5%).

EXAMPLE 29

(3aR,4S)
4,5-Dihydro-5-oxo-8-methyl-4-phenoxyacetamido-3aH azeto[1,2-a]v-triazolo[3,4-c]pyrimidine-7-carboxylate acid (41)

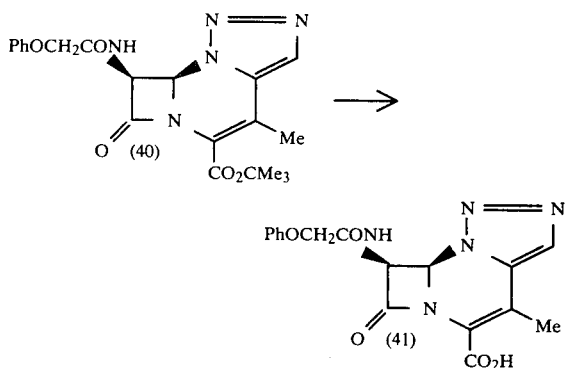

The ester [(40); 216 mg] was dissolved in trifluoroacetic acid (8 ml) and the solution kept at room temperature for 30 min. The solvent was evaporated off and the residue treated with toluene, and the mixture evaporated; this procedure was repeated. Trituration with ether gave the free acid (41) as a white amorphous solid (174 mg). $[\alpha]_D^{20.5} = -61.5°$ (c=0.93 in DMSO) $\nu$max (KBr) 3370 b, 1795 b, 1690 b cm$^{-1}$. $\delta$ppm (CDCl$_3$+D$_6$DMSO) 2.46 (3H, s), 4.35 (2H, s), 5.77 (1H, dd, J 3 Hz and 8 Hz, collapses to d J 3 Hz on exch.), 5.97 (1H, d, J 3 Hz), 6.7-7.4 (6H, m, 1H exch.), 7.88 (1H, s), 8.79 (1H, d, J 8 Hz exch.), $\lambda$max (EtOH) 301 nm ($\epsilon$7,950), 276 nm ($\epsilon$6,440). (Found: C, 54.7; H, 4.1; N, 18.4; C$_{17}$H$_{15}$N$_5$O$_5$ requires C, 55.3; H, 4.1; N, 19.0%).

The minimum inhibitory concentrations (MIC) of this compound required to inhibit the growth of various bacteria in nutrient agar are tabulated below:

| Gram-Positive Bacteria | MIC (μg/ml) |
|---|---|
| B. Subtilis | <0.2 |
| Staph. aureus Oxford | 2.5 |
| Staph. aureus Russell* | 5.0 |
| β-Haemolytic Strep. CN 10 | 0.5 |

| Gram-Negative Bacteria | MIC (μg/ml) |
|---|---|
| E. coli JT 4 | 100 |
| Ps. aeruginosa Dalgleish 10$^{-2}$ | 100 |
| Klebsiella aerogenes A | 100 |
| Enterobacter cloacae N1 | 100 |
| P. rettgeri | 100 |
| P. mirabilis C977 | >100 |
| P. morganii | >100 |

*β-lactamase producing strain

EXAMPLE 30

(3aR,4S)
4,5-Dihydro-5-oxo-8-methyl-4-D-mandelylamino-3aH-azeto[1,2-a]v-triazolo[3,4-c]pyrimidine-7-carboxylic acid (42; R=H)

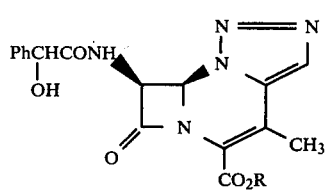

Reaction of [39; prepared from (38; 269 mg)] with D-mandelyl O-carboxyanhydride (100 mg) as described in Example 11 afforded the ester [(42; R=CMe$_3$); 166 mg]. $[\alpha]_D^{22} = -83.6°$ (C=1.05, CHCl$_3$). $\nu$max. (CHCl$_3$) 3400, 1805, 1705, 1690 (sh) cm$^{-1}$. $\delta$ppm (CDCl$_3$) 1.55 (9H, s), 2.43 (3H, s), 4.52 b (1H, d, J 3 Hz, exch.), 5.18 (1H, d, J 3 Hz, collapses to s on exch.), 5.77-6.0 (2H, m, becomes slightly broadened s at 5.85 on exch.), 7.3 (5H, s), 7.59 (1H, d, J 9 Hz, exch.), 7.65 (1H, s). $\lambda$max. (EtOH) 311 nm ($\epsilon$=8,650). (Found: C, 59.3; H, 5.6; N, 16.4. C$_{21}$H$_{23}$N$_5$O$_5$ requires C, 59.3; H, 5.4; N, 16.5%)

Treatment of [(42; R=CMe$_3$); 109 mg] with trifluoroacetic acid as described in Example 29 afforded the free acid (42; R=H) as a white amorphous solid (90 mg). $[\alpha]_D^{20} = -81.6°$ (C=0.61 in DMSO). $\nu$max. (KBr) 3360 (b), 1795, 1710, 1675 cm$^{-1}$. $\delta$ppm (D$_6$DMSO) 2.44 (3H, s), 4.95 (1H, s), 5.1-6.7 (4H, m, collapses to two d's at 5.83 and 6.0, each 1H, J 4 Hz, on exch.), 7.28 b (5H, s), b 7.88 (1H, s), 8.72 (1H, d, J 9 Hz, exch.). $\lambda$max. (0.3% NaHCO$_3$) 297 ($\epsilon$=6,300).

EXAMPLE 31

(3aR,4S) 4,5-Dihydro-5-oxo-8-methyl-4-(2-thienylacetamido)-3aH-azeto[1,2-a]y-triazolo[3,4-c]pyrimidine-7-carboxylic acid (43; R=H)

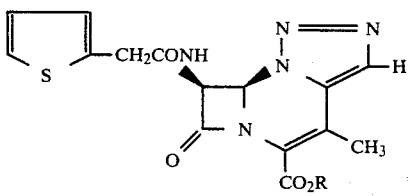

Acylation of [39; prepared from (38; 268 mg)] with 2-thienylacetyl chloride (90 mg) as described in Example 28 gave the ester [(43; R=CMe₃); 160 mg]. $[\alpha]_D^{23} = -87.2°$ (C=1, CHCl₃). νmax. (CHCl₃) 3410, 1805, 1708, 1690 (sh) cm⁻¹. δppm (CDCl₃) 1.54 (9H, s), 2.44 (3H, s), 3.75 (2H, s), 5.7–5.9 (2H, m), 6.5–6.7 (1H, m), 6.91 (2H, d), 7.2 (1H, q), 7.77 (1H, s). λmax. (EtOH) 310 nm (ε=9,070). (Found: C, 54.8; H, 5.2; N, 16.7. $C_{19}H_{21}N_5O_4S$ requires: C, 54.9; H, 5.1; N, 16.9%).

Treatment of [(43; R=CMe₃); 110 mg] with trifluoroacetic acid as described in Example 29 gave the acid (43; R=H) as a white solid (90 mg) $[\alpha]_D^{22} = -97.6°$ (C=0.4 in DMSO). νmax. (KBr) 3390, 1790, 1680 cm⁻¹. δppm (D₆DMSO). 2.41 (3H, s), 3.41 b (1H, s), 3.58 (2H, s), 5.8 (1H, dd, J 4 Hz and 9 Hz), 6.8 (1H, d, J 4 Hz), 6.8–7.0 (2H, m), 7.31 (1H, m), 8.16 (1H, s), 8.81 (1H, d, J 9 Hz). λmax. (EtOH) 298 nm (ε=8,200).

EXAMPLE 32

(3aR,4S) 4,5-Dihydro-5-oxo-8-methyl-4-DL (α-phenoxycarbonylphenyl-acetamido)-3aH-azeto[1,2-a]v-triazolo[3,4-c]pyrimidine-7-carboxylic acid (44; R=H)

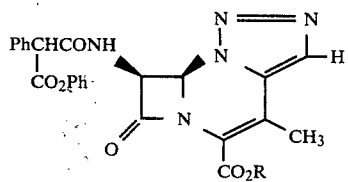

Reaction of [39; prepared from (38; 268 mg)] with freshly prepared DL-α-phenoxycarbonylphenylacetyl chloride (150 mg) as described in Example 29 afforded the amorphous ester [(44; R=CMe₃); 223 mg]. $[\alpha]_D^{20} = -39.1°$ (c=1.03, CHCl₃). νmax. 3350, 1805, 1740, 1710, 1690 (sh) cm⁻¹. δppm (CDCl₃) 1.55 (9H, s), 2.45 (3H, s), 4.69 and 4.77 (together 1H, s), 5.7–5.9 (2H,m), 6.9–7.7 (11H, m), 7.78 and 7.81 (together 1H, s). λmax (EtOH) 330 nm (ε=6,580). (Found: C, 63.6; H, 5.3; N, 13.3. $C_{28}H_{27}N_5O_6$ requires: C, 63.5; H, 5.1; N, 13.2%).

Trifluoroacetic acid treatment of [(44; R=CMe₃); 113 mg] as described in Example 29 gave the free acid (44; R=H) as a white solid (95 mg). $[\alpha]_D^{22} = -53.4°$ (C=0.86 in DMSO). νmax. (KBr) 3325, 1797, 1770 (sh) 1690 cm⁻¹. δppm (D₆DMSO). 2.43 (3H, s), 3.3 b (1H, s, exch), 4.88 and 4.92 (together 1H, s), 5.7–6.0 (1H, m), 6.12 (1H, t, overlapping doublets of β-lactam of each epimer), 7.0–7.5 (10H, m), 8.12 and 8.18 (together 1H, s), 9.05–9.3 (1H, m). λmax. (EtOH) 301 nm (ε=7,300).

EXAMPLE 33

(3aR,4S)-4,5-Dihydro-5-oxo-8-methyl-4-D-α-phenylglycylamino-3aH-azeto[1,2-a]v-triazolo[3,4-c]pyrimidine-7-carboxylic acid trifluoroacetic acid salt (46)

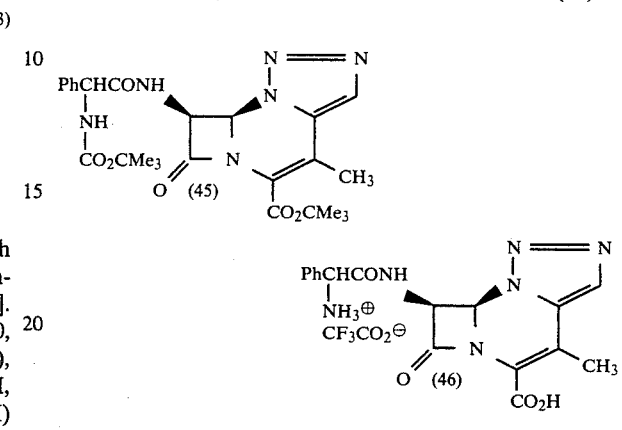

Acylation of [39; prepared from (38; 268 mg)] as described in Example 14 provided the ester (45; 260 mg). $[\alpha]_D^{20°} = -78.8°$ (C=0.95, CHCl₃). νmax. (CHCl₃) 3430, 1807, 1710, 1690 (sh) cm⁻¹. δppm (CDCl₃) 1.37 (9H, s), 1.53 (9H, s), 2.45 (3H, s), 5.25 (1H, d, J 7 Hz), 5.49 (1H, d, J 7 Hz), 5.65 (1H, dd, J 4 Hz and 9 Hz, collapses to d, J 4 Hz on esch.), 5.82 (1H, d, J 4 Hz), 7.29 (6H, m, 1 H exch.), 7.77 (1H, s). λmax. (EtOH) 310 nm (ε=8,940). (Found: C, 59.3; H, 6.1; N, 16.1. $C_{26}H_{32}N_6O_6$ requires: C, 59.5; H, 6.1; N, 16.0%).

Treatment of (45; 156 mg) with trifluoroacetic acid as described in Example 29 gave the free acid (46) as an off-white amorphous solid (133 mg). $[\alpha]_D^{20} = -65.7°$ (C=0.99 in DMSO). νmax. (KBr) 3400, 3000b, 1795, 1670b, cm⁻¹. δppm (CDCl₃+D₆DMSO) 2.44 (3H, s), 4.93 (1H, s), 3.0–5.5 (4H, very broad s, exch.) 5.7–6.2 (2H, m, collapses to two d's at 5.81 and 6.02, J 4 Hz on exch.), 7.4 (5H, s), 8.01 (1H, s), 9.24 (1H, d, J 8 Hz, exch.) λmax. (EtOH) 312 nm (ε=4,000).

EXAMPLE 34

(3aR,4S)-4,5-Dihydro-5-oxo-8-methyl-4-(2-tetrazolylacetamido)-3aH-azeto[1,2-a]v-triazolo[3,4-c]pyrimidine-7-carboxylic acid (47; R=H)

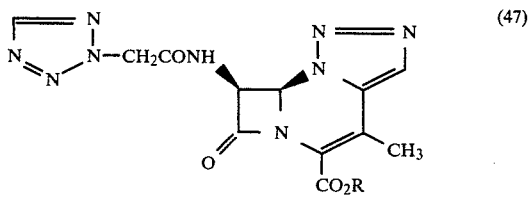

Acylation of [39; prepared from (38; 269 mg)], with freshly prepared 2-tetrazolylacetyl chloride (145 mg) as described in Example 28 gave the ester [(47; R=CMe₃); 165 mg]. $[\alpha]_D^{23} = -71.4°$ (C=0.6 in CHCl₃). νmax (CHCl₃) 3225 b, 1805, 1710, 1685 sh cm⁻¹. δppm (CDCl₃) 1.57 (9H, s), 2.43 (3H, s), 5.6 (2H, s), 5.8–6.2 (2H, m), 7.66 (1H, s), 8.29 (1H, d, J 8 Hz), 8.55 (1H, s). νmax (EtOH) 308 nm (ε=9,370). (Found: C, 48.2; H, 5.1. $C_{16}H_{19}N_9O_4$ requires C, 47.9; H, 4.7%).

Trifluoroacetic acid treatment of [(47; R=CMe₃); 145 mg] as described in Example 29 gave the free acid (47; R=H) as a white solid (118 mg). [α]$_D^{21.5}$ −65.8° (C 1.4 in DMSO). νmax. (KBr) 3320, 1793, 1705 cm⁻¹. δppm (D₆DMSO) 2.40 (3H, s), 5.42 (2H, s), 5.90 (2H, dd, J 8 Hz and 3½ Hz), 6.12 (1H, d, J 3½ Hz), 6.5–8.0b (1H, s, exch.), 8.17 (1H, s) 8.92 (1H, s), 9.26 (1H, d, J 8 Hz). λmax. (0.3% NaHCO₃) 294 nm (ε=7,050).

EXAMPLE 35

(3aR,4S)-4,5-Dihydro-5-oxo-8-methyl-4-ethylthi-oacetamido 3aH-azeto[1,2a]v-triazolo[3,4c]pyrimidine-7-carboxylic acid (48; R=H).

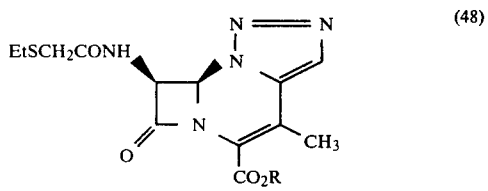

Acylation of [39; prepared from (38; 268 mg)] with freshly prepared ethylthioacetyl chloride (77 mg) as described in Example 28 afforded the ester [(48; R=CMe₃); 80 mg]. [α]$_D^{23}$ = −103.5° C. (C=1.02 in CHCl₃). νmax. (CHCl₃) 3360, 1805, 1710, 1686 cm⁻¹. δppm (CDCl₃) 1.23 (3H, t, J 7½ Hz), 1.57 (9H, s), 2.48 (3H, s), 2.59 (2H, q, J 7½ Hz), 3.2 (2H, s), 5.8–6.0 (2H, m, becomes sharp s, 5.9 on irradiation at 7.52), 7.4–7.65 (1H, m), 7.85 (1H, s). λmax. (EtOH) 311 nm (ε=8,950). (Found: C, 51.6; H, 6.0; N, 16.5. C₁₇H₂₃N₅O₄S requires: C, 51.9; H, 5.9; N, 17.8%).

Trifluoroacetic acid treatment of [(48; R=CMe₃); 75 mg] as described in Example 29 gave the free acid (48; R=H). as a white amorphous solid (45 mg). [α]$_D^{25.5}$ = −100.0° (C 1.0 in DMSO). νmax. (KBr) 3130, 1800 b, 1698, 1670 cm⁻¹. δppm 1.13 (3H, t, J 7½ Hz), 2.43 (3H, s), methylene of S—CH₂—CH₃ is obscured by solvent signals, 3.04 (2H, s), 2.7–3.7 (very broad s, 1H, exch.), 5.78 (1H, dd, J 9 Hz and 3½ Hz), 8.15 (1H, s), 8.76 (1H, d, J 9 Hz). λmax. (0.3% NaHCO₃) 296 nm (ε=9.120).

EXAMPLE 36

(3aR,4S)-4,5-Dihydro-5-oxo-8-methyl-4-cyanoacetamido 3aH-azeto[1,2a]v-triazolo[3,4-c]pyrimidine-7-carboxylic acid (49; R=H)

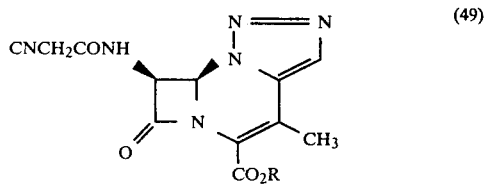

The free base [39; prepared from 38; 268 mg)] was dissolved in dry methylene chloride (5 ml) at 0° C. Dicyclohexyl-carbodiimide (113 mg) in dry methylene chloride (1 ml) was added, followed by the dropwise addition of cyanoacetic acid (46 mg) in dry DMF (1 ml). After 2 h the mixture was diluted with methylene chloride and then washed successively with dilute hydrochloric acid, dilute aqueous sodium bicarbonate and brine. The organic layer was dried and evaporated. Chromatography of the residue on silica afforded the ester [(49; R=CMe₃) 100 mg]. [α]$_D^{22}$ = −93.62° (C 0.82 in CHCl₃). νmax. (CHCl₃) 1806, 1708, 1690 sh cm⁻¹. δppm (CDCl₃) 1.56 (9H, s), 2.44 (3H, s), 3.48 (2H, s), 5.89 (2H, m, becomes sharp s on irradiation at 7.95), 7.72 (1H, s), 7.8–8.04 (1H, m). λmax. (EtOH) 306 nm (ε=10,050). (Found: C, 53.7; H, 5.0; N, 22.4. C₁₆H₁₈N₆O₄ requires: C, 53.6; H, 5.0; N, 23.5%).

Trifluoroacetic acid treatment of [(49; R=CMe₃); 60 mg] as described in Example 29 gave the acid (49; R=H) as an amorphous solid (40 mg). [α]$_D^{25.5}$ = −96.4° (C 1.04 in DMSO). νmax. (KBr) 3350 b, 1800, 1680 b cm⁻¹. δppm (D₆DMSO) 2.42 (3H, s), 3.58 (2H, s), 3.0–5.0 b (1H, s, exch.) 5.82 (1H, dd, J 8 Hz and 3½ Hz, becomes d, J 3½ Hz on exch.), 8.18 (1H, s), 9.04 (1H, d, J 8 Hz, exch.), λmax. (CH₃CN) 305 nm (ε8,700).

EXAMPLE 37

(3aR,4R)-4,5-Dihydro-5-oxo-8-methyl-4-[(2-methox-yimino-2-fur-2′-yl)acetamido]-3aH-azeto[1,2-a]v-triazolo[3,4-c]pyrimidine-7-carboxylic acid (50; R=H)

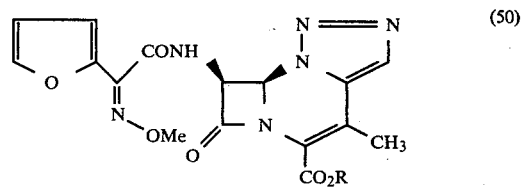

Treatment of [39; prepared from (38; 268 mg)] with dicyclohexylcarbodiimide/2-(fur-2-yl)-2-(syn)methox-yiminoacetic acid as described in Example 36 gave the ester [(50; R=CMe₃) 100 mg]. [α]$_D^{25.5}$ = −65° (C 1.04 in CHCl₃). νmax. (CHCl₃) 3400, 1806, 1710, 1690 sh, 1651 cm⁻¹. δppm (CDCl₃) 1.57 (9H, s), 2.5 (3H, s), 4.02 (3H, s), 5.9–6.10 (2H, m, becomes s, 6.0 on exch.), 6.43 (1H, dd, J 3 Hz and ca. 1½ Hz), 6.91 (1H, d, J 3 Hz), 7.38 b (1H, s, exch.), 7.45 (1H, d, J ca. 1½ Hz), 7.86 (1H, s). λmax. (EtOH) 285 nm (ε=17,400).

Deprotection of [(50; R=CMe₃); 90 mg] with trifluoroacetic acid as described in Example 29 afforded the acid (50; R=H) as a white powder (60 mg). [α]$_D^{21.5}$ = −12.3° (C=1.0 in DMSO). νmax. (KBr) 3350, 1800, 1678 cm⁻¹. δppm D₆DMSO) 2.4 (3H, s), 3.32 b (1H, s, exch.), 3.84 (3H, s), 5.95 (1H, dd, J 8 Hz and 3½ Hz, becomes d, J 3½ Hz on irradiation at 9.48), 6.2 (1H, d, J 3½ Hz), 6.6 (1H, m), 6.79 (1H, d, J 3 Hz), 7.77 (1H, slightly broadened s), 8.18 (1H, s), 9.43 (1H, d, J 8 Hz). λmax. (1% NaHCO₃) 288 nm (ε=19,800).

EXAMPLE 38

(3aR,4S)-4,5-Dihydro-5-oxo-8-methyl-4-trifluoroacetamido 3aH-azeto[1,2-a]v-triazolo[3,4-c]pyrimidine-7-carboxylic acid (51; R=H).

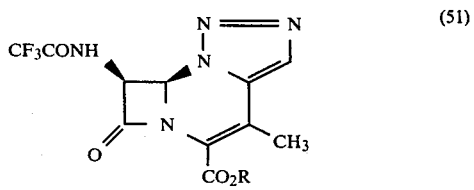

The free base [39; prepared from (38; 269 mg)] was dissolved in dry methylene chloride (5 ml) and triethylamine (76 mg) added, followed by the dropwise addition of trifluoroacetic anhydride (158 mg) in dry methylene chloride (5 ml). The mixture was washed successively with dilute hydrochloric acid, dilute aqueous sodium hydrogen carbonate and brine, dried and evaporated. Chromatography on silica afforded the ester (51; R=CMe$_3$) as an amorphous solid (117 mg). $[\alpha]_D^{22} = -106.1°$ (C 1.0 in CHCl$_3$) $\nu$max. (CHCl$_3$), 1806, 1710 b cm$^{-1}$. $\delta$(CDCl$_3$)1.57 (9H, s), 2.57 (3H, s), 3.9–4.14 (2H, m), 7.75 (1H, s), 8.06 (1H, d, J 9 Hz) $\lambda$max. (EtOH) 307 nm ($\epsilon$=10,200).

Deprotection of [(51; R=CMe$_3$); 75 mg] with trifluoroacetic acid as described in Example 29 provided the acid (51; R=H) as a white solid (55 mg). $[\alpha]_D^{25.5} = -128.2°$ (c 1.0 in DMSO). $\nu$max. (KBr) 3290, 1800, 1718 cm$^{-1}$. $\delta$ppm (D$_6$DMSO) 2.42 (3H, s), 2.7–3.7 (1H, m, exch.), 5.94 (1H, dd, J 8 Hz and 3½ Hz, becomes d, J 3½ Hz on exch.), 4.18 (1H, d, J 3½ Hz), 8.18 (1H, s), 10.2 (1H, d, J 8 Hz exch.). $\lambda$max. (CH$_3$CN) 304 nm ($\epsilon$=10,350).

EXAMPLE 39

(3a,4S) t-Butyl 4,5-dihydro-5-oxo-8-bromomethyl-4-triphenylmethylamino 3aH-azeto[1,2-a]v-triazolo[3,4-c]pyrimidine-7-carboxylate (52)

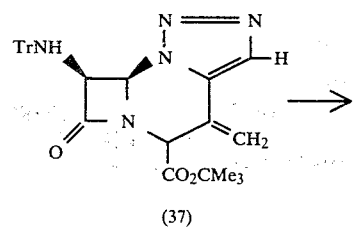

The lactam (37; 618 mg) was dissolved in dry tetrahydrofuran (40 ml) containing dibromodiethylmalonate (400 mg). The solution, under argon, was cooled to −76° and 1,5-diazabicyclo[5.4.0]undec-5-ene (193 mg) in dry tetrahydrofuran (10 ml) added dropwise over 10 minutes. The solution was poured into ethyl acetate—very dilute hydrochloric acid and the organic layer separated, washed with brine, dried and evaporated. Chromatography on silica afforded the bromo-derivative (52) as a white crystalline solid. (486 mg). m.p. 162°–163° dec. (ether trituration) $[\alpha]_D^{20} = -27.6°$ (C=1, CHCl$_3$). $\nu$max. (CHCl$_3$) 3350, 1805, 1712 cm$^{-1}$. $\delta$ppm (CDCl$_3$) 1.38 (9H, s), 3.10 (1H, d, J 9 Hz exch.), 4.40 and 4.68 (2H, Abq, J 10 Hz), 4.78–5.0 (2H, m, collapses to s at 4.92 on exch.), 6.9–7.5 (15H, m), $\lambda$max. (EtOH) 320 nm ($\epsilon$=8,640). (Found: C, 63.1; H, 5.2; N, 11.4, Br, 13.3. C$_{32}$H$_{30}$N$_5$O$_3$Br requires: C, 62.7; H, 4.9; N, 11.4; Br, 13.1%).

EXAMPLE 40

(3aR,4S) t-Butyl, 4,5-dihydro-5-oxo-8-acetoxymethyl-4-triphenylmethylamino-3aH-azeto[1,2-a]v-triazolo[3,4-c]pyrimidine-7-carboxylate (54)

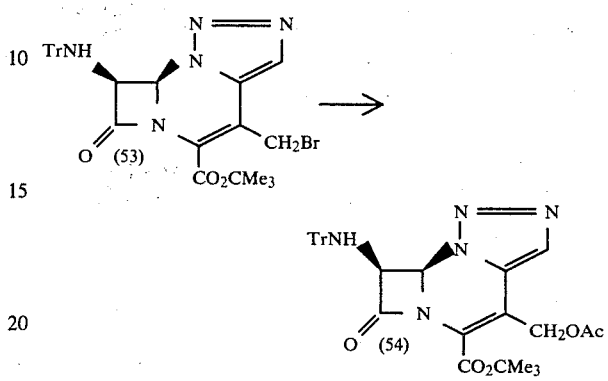

The lactam (53; 314 mg) was dissolved in chloroform (10 ml) (dried by passage through basic alumina) and tetraethylammonium acetate (200 mg) added. The mixture was stirred in the dark for 21 h and then washed with dilute hydrochloric acid, brine, dried and evaporated. Chromatography on silica afforded (54) as an amorphous solid (255 mg) $[\alpha]_D^{21} = -19.3°$ (C=1 in CHCl$_3$). $\nu$max (CHCl$_3$) 3350, 1802, 1740, 1715 cm$^{-1}$. $\delta$ppm (CDCl$_3$) 1.5 (9H, s), 2.03 (3H, s), 3.28 (1H, d, J 10 Hz exch.), 4.95–5.15 (2H, m, collapses to s at 5.08 on exch.), 5.09 and 5.58 (2H, ABq, J 14 Hz), 7.0–7.75 (15H, m), 7.89 (1H, s). $\lambda$max (EtOH) 311 nm ($\epsilon$=9,350). (Found: C, 69.0; H, 5.7; N, 11.6. C$_{34}$H$_{33}$N$_5$O$_5$ requires C, 69.0; H, 5.6; N, 11.8%).

EXAMPLE 41

(3aR,4S) t-Butyl 4,5-dihydro-5-oxo-8-acetoxymethyl-4-(2-thienylacetamido)-3aH-azeto[1,2-a]v-triazolo[3,4-c]pyrimidine-7-carboxylate (56)

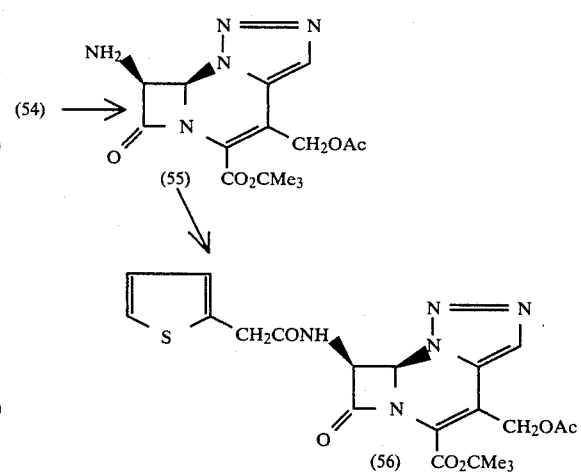

The lactam (54; 261 mg) was dissolved in dry methylene chloride (8 ml) and the solution cooled to −20°. Toluene-p-sulphonic acid (92 mg) was then added in the minimum volume of methanol and the solution kept at 4° C. for 18 h. The solvents were removed and the residue dissolved in ethyl acetate—sodium hydrogen carbonate. The organic layer was separated, washed with brine, dried, and evaporated to give (55). The latter was acylated with 2-thienylacetyl chloride (70 mg) as described in Example 28, to provide (56; 58 mg). $[\alpha]_D^{21.5} = -136.7°$ (C=0.39 in CHCl$_3$). νmax (CHCl$_3$) 3415, 1810, 1740, 1713, 1689 cm$^{-1}$. δppm (CDCl$_3$) 1.58 (9H, s), 2.08 (3H, s), 3.77 (2H, s), 5.17 and 5.7 (2H, ABq, J 14 Hz), 5.6–6.0 (2H, m), 6.82–7.41 (3H, m), 7.9 (1H, s). λmax. (EtOH) 315 nm (ε=9,370).

EXAMPLE 42

(3aR,4S) 4,5-Dihydro-5-oxo-8-acetoxymethyl-4-(2-thienylacetamido)-3aH-azeto[1,2-a]v-triazolo[3,4-c]pyrimidine-7-carboxylic acid (57)

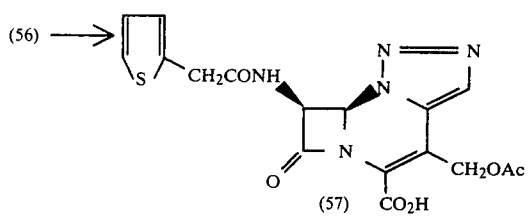

The ester (56; 35 mg) was treated with trifluoroacetic acid (2 ml) as described in Example 29 to provide the free acid (57) as a tan coloured solid (28 mg). $[\alpha]_D^{21.5} = -115.1°$ (C=0.23 in DMSO). νmax. (KBr) 3350, 1805, 1725, 1675 cm$^{-1}$. δppm (D$_6$DMSO) 2.03 (3H, s) 3.58 (2H, s), 3.75–5.25 b (1H, s, exch.), 5.16 and 5.42 (2H, ABq, J 13 Hz), 5.83 (1H, dd, J 8 Hz and 3½ Hz), 6.13 (1H, d, J 3½ Hz), 6.75–7.40 (3H, m), 8.1 (1H, s), 8.85 (1H, d, J 8 Hz), λmax (0.3% NaHCO$_3$) 300 nm (ε=6,630).

EXAMPLE 43

(3aR,4S) t-Butyl 4,5-dihydro-5-oxo-8-[5-methyl(1,3,4-thiadiazol-2-yl)thiomethyl]-4-triphenylmethylamino-3aH-azeto[1,2-a]v-triazolo[3,4-c]pyrimidine-7-carboxylate (58)

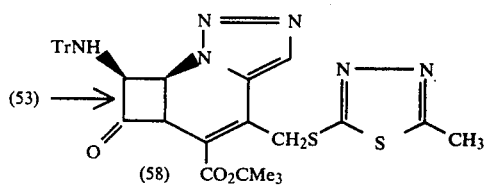

The lactam (53; 306 mg) was dissolved in dry methylene chloride (10 ml) and 5-methyl-2-mercapto-1,3,5-thiadiazole (80 mg) added. The solution was cooled to −20° and triethylamine (60 mg) in methylene chloride (2 ml) added. The reaction was allowed to warm to room temperature and was then washed with dilute hydrochloric acid, brine, dried and evaporated. Chromatography on silica afforded the ester (58) as an amorphous solid (288 mg). $[\alpha]_D^{20} = -60.1°$ (C=0.89 in CHCl$_3$). νmax. (CHCl$_3$) 3350, 1802, 1710 cm$^{-1}$. δppm (CDCl$_3$) 1.5 (9H, s), 2.65 (3H, s), 3.23 (1H, d, exch.), 4.58 and 4.98 (2H, ABq, J 13 Hz), 4.9–5.1 (2H, m, collapses to s at 5.0 on exch.), 7.0–7.7 (15H, m), 8.04 (1H, s). λmax. (EtOH) 316 nm (ε=8,900). (Found: C, 63.0; H, 5.2; N, 14.3. C$_{35}$H$_{33}$N$_7$O$_3$S$_3$ requires: C, 63.3; H, 5.0; N, 14.8%).

EXAMPLE 44

(3aR,4S) t-Butyl 4,5-dihydro-5-oxo-8-[5-methyl(1,3,4-thiadiazol-2-yl)thiomethyl]-4-(2-thienylacetamido)-3aH-azeto[1,2-a]v-triazolo[3,4-c]pyrimidine-7-carboxylate (59)

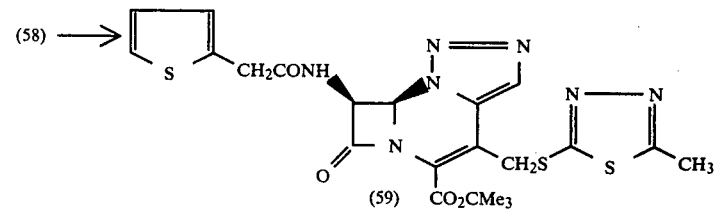

Detritylation and acylation of (58; 221 mg) as described in Example 41 gave (59; 115 mg). $[\alpha]_D^{22} = -130.8°$ (C 1.0 in CHCl$_3$). νmax. (CHCl$_3$) 3410, 1805, 1700 b cm$^{-1}$. δppm (CDCl$_3$) 1.56 (9H, s), 2.71 (3H, s), 3.76 (2H, s), 4.62 and 5.09 (2H, ABq, J 13 Hz), 5.72–5.89 (2H, m), 6.55 (1H, d, J 7½ Hz), 6.92–7.26 (3H, m), 8.05 (1H, s). λmax. 321 nm (ε=9.360). (Found: C, 48.4; H, 4.0; N, 17.2. C$_{22}$H$_{23}$N$_7$O$_4$S$_3$ requires: C, 48.4; H, 4.2; N, 18.0%).

EXAMPLE 45

(3aR,4S) 4,5-Dihydro-5-oxo-8-[5-methyl(1,3,4-thiadiazol-2-yl)thiomethyl]-4-(2-thienylacetamido)-3aH-azeto[1,2-a]-v-triazolo[3,4-c]pyrimidine-7-carboxylic acid (60)

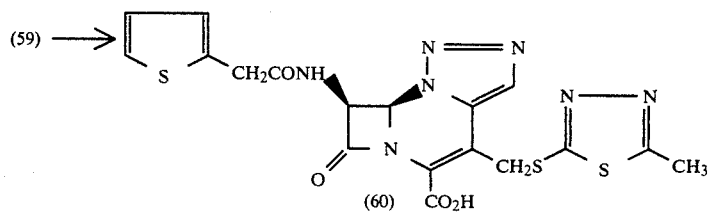

The ester (59; 69 mg) was treated with trifluoroacetic acid (2 ml) as described in Example 29 to give the acid (60) as a pale green-gray solid (62 mg). $[\alpha]_D^{21.5} = -157.6°$ (C=0.79 in DMSO). $\nu$max (KBr) 3370, 1800, 1710 sh, 1680 cm$^{-1}$. δppm (D$_6$DMSO) 2.67 (3H, s), 3.48 and 3.68 (2H, ABq, J 16 Hz), 3.20–3.7 b (1H, s, exch.), 4.57 and 5.03 (2H, ABq, J 14 Hz), 5.74 (1H, dd, J 8 Hz and 3½ Hz, becomes d, J 3½ Hz on exch.), 6.06 (1H, d, J 3½ Hz), 6.8–7.4 (3H, m), 8.18 (1H, s), 8.88 (1H, d, J 8 Hz, slowly exch.). λmax. (0.3% NaHCO$_3$) 300 nm (ε=7,500). The antibacterial activity of the compounds described in Examples 30–38, 42 and 45 are set out in Tables 1 and 2.

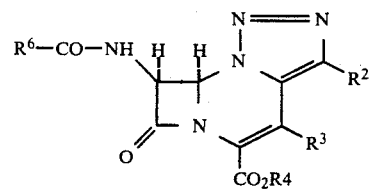

or a salt thereof, wherein R$^2$ is hydrogen, lower alkyl, phenyl, p-nitrophenyl, p-methoxycarbonylphenyl, R$^3$ is hydrogen, lower alkyl, substituted lower alkyl, R$^6$CO is of the sub-formulae (a)–(d):

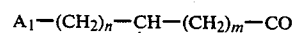 (a)

 (b)

TABLE 1

| | MIC (μg/ml)* | | | | | | |
|---|---|---|---|---|---|---|---|
| | Compounds (R = H) | | | | | | |
| Organism | 42 | 43 | 44 | 46 | 47 | 57 | 60 |
| E. coli JT 4 | >100 | >100 | >100 | >100 | >100 | >100 | >100 |
| K. aerogenes A | >100 | 50 | 50 | >100 | >100 | >100 | >100 |
| E. cloacae N1 | >100 | >100 | >100 | >100 | >100 | >100 | >100 |
| P. rettgeri | >100 | >100 | >50 | >100 | >100 | >100 | >100 |
| P. mirabilis C 977 | >100 | 10 | 50 | >100 | >100 | >100 | >100 |
| P. morganii | 100 | >100 | >100 | >100 | >100 | >100 | >100 |
| B. subtilis | 1 | <0.2 | 25 | 100 | 0.5 | 100 | 50 |
| S. aureus Oxford 25 | 1 | 50 | >100 | 2.5 | >100 | >100 | |
| S. aureus Russell | >100 | 2.5 | 100 | >100 | 5.0 | >100 | >100 |
| S. aureus 1517 | >100 | 2.5 | >100 | >100 | >100 | >100 | >100 |
| S. faecalis 1 | >100 | 2.5 | >100 | >100 | 50 | >100 | >100 |
| S. pyogenes CN 10 | — | <0.2 | — | — | 1.0 | >100 | >100 |

*Serial dilution in nutrient agar containing 5% horse blood, inoculum 0.001 ml undiluted broth culture.

TABLE 2

| | MIC (μg/ml)* | | | | | | |
|---|---|---|---|---|---|---|---|
| | Compounds (R = H) | | | | | | |
| Compounds | 43 | 44 | 48 | 49 | 50 | 51 | 60 |
| E. coli 0111 | 10 | 10 | 50 | 100 | 100 | 100 | >100 |
| K. aerogenes A | 2.5 | 10 | 50 | 100 | 100 | >100 | >100 |
| E. cloacae N1 | >100 | 50 | >100 | >100 | >100 | >100 | >100 |
| P. rettgeri WM 16 | >100 | 10 | >100 | >100 | >100 | >100 | >100 |
| P. mirabilis C 977 | 2.5 | 10 | 10 | 50 | 50 | >100 | >100 |
| P. morganii 1580 | 2.5 | 10 | 25 | 100 | 100 | >100 | >100 |
| B. subtilis | ≦0.2 | 25 | 0.2 | 2.5 | 5.0 | 5.0 | 5.0 |
| S. aureus Oxford | 2.5 | 25 | —$^c$ | 5.0 | —$^c$ | >100 | —$^c$ |
| S. aureues Russell | 1.0 | 25 | 5.0 | 25 | 25 | >100 | 25 |
| S. aureus 1517 | 5.0 | 100 | 25 | 100 | 100 | >100 | 100 |
| S. faecalis 1 | 5.0 | >100 | 25 | 25 | >100 | 100 | 25 |
| S. pneumoniae CN 33 | ≦0.2 | 10 | 1.0 | 5.0 | 10 | 50 | 0.5 |
| S. pyogenes CN 10 | ≦0.2 | 10 | 0.5 | 2.5 | 1.0 | 25 | 2.5 |

*Serial dilution in DST agar containing 10% horse blood, inoculum 0.001 ml broth culture diluted 10$^{-2}$ for Gram-positive and 10$^{-4}$ for Gram-negative organisms.
—$^c$ Culture contaminated

I claim:
1. A compound of the formula (II):

-continued

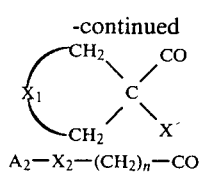 (c)

A$_2$—X$_2$—(CH$_2$)$_n$—CO (d)

wherein n is 0, 1 or 2; m is 0, 1 or 2; A$_1$ is C$_1$–C$_6$ alkyl, C$_3$–C$_6$ cycloalkyl, cyclohexenyl, cyclohexadienyl, phenyl, hydroxy-phenyl, thienyl or pyridyl group; x is a hydrogen or halogen atom, a carboxylic acid, a carboxylic acid ester, azido, tetrazolyl, hydroxy, acyloxy, amino, ureido, guanidino or acylureido group; A$_2$ is a phenyl, a 2,6-dimethoxyphenyl, 2-alkoxy-1-naphthyl, 3-arylisoxazoyl or 3-aryl-5-methylisoxazolyl group; X$_1$ is a CH$_2$OCH$_2$, CH$_2$SCH$_2$ or (CH$_2$)$_n$ group; and X$_2$ is an oxygen or sulphur atom and CO$_2$R$^4$ is a carboxylic acid group or a pharmaceutically acceptable salt or tert-butyl, benzyl or p-nitrobenzyl ester thereof.

2. A compound of the formula II:

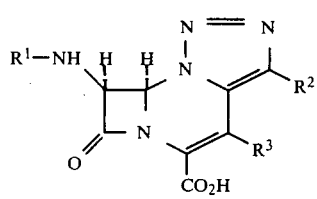 (II)

or a salt thereof wherein R$^1$ is hydrogen, a trityl group or a group R$_6$CO, R$^2$ is hydrogen, lower alkyl, phenyl, p-nitrophenyl, p-methoxycarbonylphenyl, R$^3$ is hydrogen, lower alkyl, substituted lower alkyl or thiosubstituted lower alkyl and said R$_6$CO is of the sub-formulae (a)-(d):

A$_1$—(CH$_2$)$_n$—CH—(CH$_2$)$_m$—CO (a)
A$_2$—CO (b)
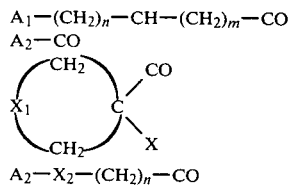 (c)
A$_2$—X$_2$—(CH$_2$)$_n$—CO (d)

wherein n is 0, 1 or 2; m is 0, 1 or 2; A$_1$ is C$_1$–C$_6$ alkyl, C$_3$–C$_6$ cycloalkyl, cyclohexenyl, cyclohexadienyl, phenyl, hydroxy-phenyl, thienyl or pyridyl group; x is a hydrogen or halogen atom, a carboxylic acid, a carboxylic acid ester, azido, tetrazolyl, hydroxy, acyloxy, amino, ureido, guanidino or acylureido group; A$_2$ is a phenyl, a 2,6-diamethoxyphenyl, 2-alkoxy-1-naphtyl, 3-arylisoxazoyl or 3-aryl-5-methylisoxazolyl group; X$_1$ is a CH$_2$OCH$_2$, CH$_2$SCH$_2$ or (CH$_2$)$_n$ group; and X$_2$ is an oxygen or sulphur atom.

3. A compound as claimed in claim 2 wherein R$^2$ is a hydrogen atom.

4. A compound as claimed in claim 2 wherein R$^3$ is a methyl group.

5. A compound as claimed in claim 2 of the formula (III):

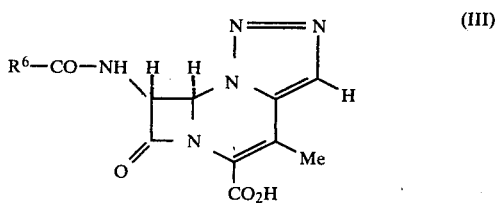 (III)

or a salt thereof wherein R$^6$CO is of the sub-formulae (a)-(d):

A$_1$—(CH$_2$)$_n$—CH—(CH$_2$)$_m$—CO (a)
A$_2$—CO (b)
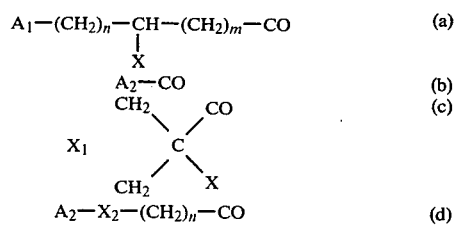 (c)
A$_2$—X$_2$—(CH$_2$)$_n$—CO (d)

wherein n is 0, 1 or 2; m is 0, 1 or 2; A$_1$ is C$_1$–C$_6$ alkyl, C$_3$–C$_6$ cycloalkyl, cyclohexenyl, cyclohexadienyl, phenyl, hydroxy-phenyl, thienyl or pyridyl group; x is a hydrogen or halogen atom, a carboxylic acid, carboxylic ester, azido, tetrazolyl, hydroxy, acyloxy, amino, ureido, guanidino or acylureido group; A$_2$ is a phenyl, a 2,6-dimethoxyphenyl, 2-alkoxy-1-naphthyl, 3-arylisoxazoyl or 3-aryl-5-methylisoxazolyl group; X$_1$ is a CH$_2$OCH$_2$, CH$_2$SCH$_2$ or (CH$_2$)$_n$ group; and X$_2$ is an oxygen or sulphur atom.

6. A compound as claimed in claim 5 wherein R$^6$ is a group of the sub-formulae (e) or (f):

wherein R$^7$ is a phenyl, thienyl or phenoxy group; R$^8$ is a hydrogen atom or methyl group; R$^9$ is a phenyl, p-hydroxyphenyl, thienyl or cyclohexadienyl group; and R$^{10}$ is a hydroxyl, amino or carboxylic acid group or a lower alkyl or phenyl, tolyl or indanyl ester thereof.

7. A compound as claimed in claim 5 wherein R$^6$CO is a D-phenylglycyl, D-p-hydroxyphenylglycyl, D-mandelyl, malonyl, benzoyl, 2-thienylacetyl, 3-thienylacetyl, 2-thienyl-α-carboxyacetyl, 3-thienyl-α-carboxyacetyl or phenoxyacetyl group.

8. A compound as claimed in claim 2 wherein R$^1$ is a hydrogen atom.

9. A compound as claimed in claim 2 wherein R$^1$ is a trityl group.

10. An antibacterial pharmaceutical composition which comprises an antibacterially effective amount of a compound as claimed in claim 2 and a pharmaceutically acceptable carrier therefor.

* * * * *